United States Patent
Stephen et al.

(10) Patent No.: US 11,613,560 B2
(45) Date of Patent: Mar. 28, 2023

(54) BICYCLIC PEPTIDE LIGANDS SPECIFIC FOR OX40

(71) Applicant: BicycleTx Limited, Cambridge (GB)

(72) Inventors: Tom Li Stephen, Cambridge (GB);
Kevin McDonnell, Lexington, MA (US); Nicholas Keen, Carlisle, MA (US); Liuhong Chen, Cambridge (GB); Helen Harrison, Cambridge (GB); Peter U. Park, Lexington, MA (US); Michael Skynner, Cambridge (GB); Harvey Che, Cambridge (GB)

(73) Assignee: BicycleTx Limited, Cambridge (GB)

(*) Notice: Subject to any disclaimer, the term of this patent is extended or adjusted under 35 U.S.C. 154(b) by 205 days.

(21) Appl. No.: 16/872,097

(22) Filed: May 11, 2020

(65) Prior Publication Data
US 2020/0354406 A1   Nov. 12, 2020

Related U.S. Application Data

(60) Provisional application No. 62/845,473, filed on May 9, 2019.

(51) Int. Cl.
*C07K 7/56* (2006.01)
*A61K 47/64* (2017.01)

(52) U.S. Cl.
CPC .............. *C07K 7/56* (2013.01); *A61K 47/645* (2017.08)

(58) Field of Classification Search
CPC ................................ A61K 47/645; C07K 7/56
See application file for complete search history.

(56) References Cited

U.S. PATENT DOCUMENTS

| | | |
|---|---|---|
| 8,685,890 B2 | 4/2014 | Winter et al. |
| 9,868,767 B2 | 1/2018 | Pei et al. |
| 10,875,894 B2 | 12/2020 | Chen et al. |
| 10,919,937 B2 | 2/2021 | Beswick et al. |
| 11,306,123 B2 | 4/2022 | Mudd et al. |
| 11,312,749 B2 | 4/2022 | Mudd et al. |
| 11,332,500 B2 | 5/2022 | Mudd et al. |
| 2005/0169931 A1 | 8/2005 | Kinch et al. |
| 2017/0190743 A1 | 7/2017 | Pei et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2020/0255477 A1 | 8/2020 | Chen et al. |
| 2020/0338203 A1 | 10/2020 | Chen et al. |
| 2020/0354406 A1 | 11/2020 | Stephen et al. |
| 2021/0040154 A1 | 2/2021 | Mudd et al. |
| 2021/0069287 A1 | 3/2021 | Mudd et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0147484 A1 | 5/2021 | Beswick et al. |
| 2021/0261620 A1 | 8/2021 | Teufel et al. |
| 2021/0299210 A2 | 9/2021 | Keen et al. |
| 2022/0184222 A1 | 6/2022 | Bennett et al. |

FOREIGN PATENT DOCUMENTS

| | | |
|---|---|---|
| WO | WO-2004077062 A2 | 9/2004 |
| WO | WO-2009098450 A2 | 8/2009 |
| WO | WO-2010089115 A1 | 8/2010 |
| WO | WO-2012057624 A1 | 5/2012 |
| WO | WO-2016067035 A1 | 5/2016 |
| WO | WO-2017173408 A1 | 10/2017 |
| WO | WO-2017182672 A1 | 10/2017 |
| WO | WO-2017191460 A1 | 11/2017 |
| WO | WO-2018115203 A1 | 6/2018 |
| WO | WO-2018156740 A1 | 8/2018 |
| WO | WO-2019025811 A1 | 2/2019 |
| WO | WO-2019122860 A1 | 6/2019 |
| WO | WO-2019122861 A1 | 6/2019 |
| WO | WO-2019122863 A1 | 6/2019 |
| WO | WO-2019162682 A1 | 8/2019 |
| WO | WO-2019193328 A1 | 10/2019 |
| WO | WO-2019243313 A1 | 12/2019 |

(Continued)

OTHER PUBLICATIONS

Upadhyaya, "Activation of CD137 Using Multivalent and Tumour Targeted Bicyclic Peptides," URL:https://www.bicycletherapeutics.com/wp-content/uploads/PU_2019-Peptide-Congress_publication.pdf; Apr. 25, 2019.
Anonymous, "Constrained Peptides Unconstrained Thinking Forward-Looking Statements," URL:https://investors.bicycletherapeutics.com/static-files/1e4832c5-1181-4fcc-acd9-c1dbblc8b594, Aug. 1, 2019.
Chen, "The Bicycle Platform: an Efficient Technology to Generate High Affinity, High Selectivity Molecules (Bicycles) With Unique Drug Like Properties That Are Amenable to Conjugation," URL:https://www.bicycletherapeutics.com/wp-content/uploads/16_PEGS-Bicycle_-30-04-2017-poster.pdf, Apr. 26, 2017.
Linch et al., "OX40 Agonists and Combination Immunotherapy: Putting the Pedal to the Metal," Frontiers in Oncology, vol. 5, No. 34, Feb. 16, 2015, pp. 1-14.

(Continued)

*Primary Examiner* — Li N Komatsu
(74) *Attorney, Agent, or Firm* — Dechert LLP; Andrea L. C. Reid; Gang Wang

(57) ABSTRACT

The present invention relates to polypeptides which are covalently bound to molecular scaffolds such that two or more peptide loops are subtended between attachment points to the scaffold. In particular, the invention describes peptides which bind to OX40. The invention also relates to multimeric binding complexes of polypeptides which are covalently bound to molecular scaffolds such that two or more peptide loops are subtended between attachment points to the scaffold that are functional agonists of OX40. The invention also includes drug conjugates comprising said peptides and complexes, conjugated to one or more effector and/or functional groups, to pharmaceutical compositions comprising said peptide ligands, complexes and drug conjugates and to the use of said peptide ligands and drug conjugates in preventing, suppressing or treating a disease or disorder mediated by OX40.

26 Claims, 2 Drawing Sheets

Specification includes a Sequence Listing.

(56) References Cited

FOREIGN PATENT DOCUMENTS

| WO | WO-2019243832 A1 | 12/2019 |
|---|---|---|
| WO | WO-2019243833 A1 | 12/2019 |
| WO | WO-2020084305 A1 | 4/2020 |
| WO | WO-2020128526 A1 | 6/2020 |
| WO | WO-2020201753 A1 | 10/2020 |
| WO | WO-2020225577 A1 | 11/2020 |
| WO | 2021019243 | 2/2021 |
| WO | 2021019246 | 2/2021 |
| WO | WO-2021019243 A1 | 2/2021 |
| WO | WO-2021019245 A1 | 2/2021 |
| WO | WO-2021064428 A1 | 4/2021 |
| WO | WO-2021105694 A1 | 6/2021 |
| WO | WO-2021250418 A1 | 12/2021 |

OTHER PUBLICATIONS

PCT International Search Report and Written Opinion for PCT Application No. PCTGB2020/051144, mailed by the ISA/EP dated Aug. 18, 2020, 16 Pages.

U.S. Appl. No. 17/630,747, filed Jan. 27, 2022.

U.S. Appl. No. 17/590,875, filed Feb. 2, 2022.

U.S. Appl. No. 17/592,966, filed Feb. 4, 2022.

Annunziata et al., "Phase 1, open-label study of MEDI-547 in patients with relapsed or refractory solid tumors," Invest New Drugs. Feb. 2013;31(1):77-84.

Bennett et al., "Abstract 5855: Bicycle Drug Conjugates Targeting EphA2 for the Treatment of Solid Tumors: Discovery and Selection of BT5528," Cancer Res. 2018;78(13 suppl):5855.

Bennett et al., "Development of BT1718, a Bicycle Drug Conjugate® (BDC) targeting MT1-MMP for treatment of solid tumours," Eur J Cancer. Dec. 2016;69(suppl 1):S21(42;P013).

Bennett, "BT5528, an EphA2-targeting Bicycle® Toxin Conjugate (BTC): Profound efficacy without bleeding and coagulation abnormalities in animal models," AACR Annual Meeting 2019. 4481.

Bicycle Therapeutics, Press Release—MarketWatch.com, Apr. 2018.

Chen et al., "Peptide Ligands Stabilized by Small Molecules," Angew. Chem. Int. Ed., 2014, vol. 53, pp. 1602-1606.

Deonarain et al., "Small-Format Drug Conjugates: A Viable Alternative to ADCs for Solid Tumours?" Antibodies (Basel). 2018;7(2):16.

Deyle et al., "Phage Selection of Cyclic Peptides for Application in Research and Drug Development," Accounts of Chemical Research, 2017, vol. 50(8), pp. 1866-1874.

Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13 suppl):5144.

Heinis et al., "Phage-encoded combinatorial chemical libraries based on bicyclic peptides," Nat Chem Biol. Jul. 2009;5(7):502-7.

Hurov et al., "BT7480, a novel fully synthetic tumor-targeted immune cell agonist (TICA ™) induces tumor localized CD137 agonism." https://www.bicycletherapeutics/com/wp-content/uploads/2020-06-16-BT7480-AaCR-2020-poster-P5552_Final_CD137-in-title-002.pdf2020.

International Search Report and Written Opinion for International Application No. PCT/GB2020/051827, dated Nov. 3, 2020, 11 Pages.

Loktev et al., "Multicyclic Peptides as Scaffolds for the Development of Tumor Targeting Agents," Current Medicinal Chemistry, 2017, vol. 24, pp. 2141-2155.

Mitra et al., "Structure-Activity Relationship Analysis of Peptides Targeting the EphA2 Receptor," Biochemistry. 2010;49(31):6687-95.

Morrison, "Chemical Strategies for Bicyclic Peptide Formation," Univ. of Leeds, Sep. 2015, pp. 1-60.

Mudd et al., "Identification and Optimization of EphA2-Selective Biccyles for the Delivery of Cytotoxic Payloads," J Med Chem. 2020; 63(8) 4107-4116.

Mulder et al., "Scaffold Optimization in Discontinuous Epitope Containing Protein Mimics of gp120 Using Smart Libraries," Org. Biomol. Chem. 2013, vol. 11, pp. 2676-2684.

PCT International Search Report and Written Opinion for PCT/GB2018/053678 dated Mar. 20, 2019.

PCT International Search Report for PCT Application No. PCT/EP2019/065993, mailed by the European Patent Office dated Sep. 24, 2019, 5 Pages.

PCT International Search Report for PCT Application No. PCT/GB2020/051829, mailed by the European Patent Office dated Oct. 30, 2020, 5 Pages.

Pickens et al., "Practical Considerations, Challenges and Limitations of Bioconjugation via Azide-Alkyne Cycloaddition," Bioconjugate Chem., 2018, vol. 29, pp. 686-701.

Rhodes et al., Chemistry—A European Journal, vol. 23, No. 52, Sep. 2017, pp. 12690-12703.

Shi et al., "One-Bead-Two-Compound Thioether Bridged Macrocyclic [gamma] -AApeptide Screening Library Against EphA2," J. Med. Chem. 2017;60(22):9290-9298.

Smeenk et al., "Reconstructing the Discontinuous and Conformational β1/β3-Loop Binding Site on hFSH/hCG by Using Highly Constrained Multicyclic Peptides," ChemBioChem 2015, vol. 16, pp. 91-99.

Upadhyaya, "Activation of CD137 Using Multivalent and Tumour Targeted Bicyclic Peptides," URL:https://www.bicycletherapeutics.com/wp-content/uploads/PU_2019-Peptide-Congress_publication.pdf, Peptide Congress, Apr. 25, 2019, 25 Pages.

Wu et al., "Design and Characterization of Novel EphA2 Agonists for Targeted Delivery of Chemotherapy to Cancer Cells," Chem. Biol. 2015;22(7):876-887.

SEQUENCE LISTING

```
<160> NUMBER OF SEQ ID NOS: 73

<210> SEQ ID NO 1
<211> LENGTH: 13
<212> TYPE: PRT
<213> ORGANISM: Artificial
<220> FEATURE:
<223> OTHER INFORMATION: Synthetic Peptide

<400> SEQUENCE: 1

Cys Ile Leu Trp Cys Leu Pro Glu Pro His Asp Glu Cys
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is K or S
<220> FEATURE:
<221> NAME/KEY: Xaa
<222> LOCATION: (4)..(4)
<223> OTHER INFORMATION: Xaa is N or E
```

<400> SEQUENCE: 2

Cys Ala Xaa Xaa Cys Asp Pro Phe Trp Tyr Gln Phe Tyr Cys
1               5                   10

<210> SEQ ID NO 3
<211> LENGTH: 14
<212> TYPE: PRT
<213> ORGANISM: Artificial
<220> FEATURE:
<223> OTHER INFORMATION: Synthetic Peptide

<400> SEQUENCE: 3

Cys Ala Lys Asn Cys Asp Pro Phe Trp Tyr Gln Phe Tyr Cys
1               5                   10

<210> SEQ ID NO 4
<211> LENGTH: 14
<212> TYPE: PRT
<213> ORGANISM: Artificial
<220> FEATURE:
<223> OTHER INFORMATION: Synthetic Peptide

<400> SEQUENCE: 4

Cys Ala Ser Glu Cys Asp Pro Phe Trp Tyr Gln Phe Tyr Cys
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is L or N
<220> FEATURE:
<221> NAME/KEY: Xaa
<222> LOCATION: (12)..(12)
<223> OTHER INFORMATION: Xaa is D or K

<400> SEQUENCE: 5

Cys Xaa Tyr Ser Pro Cys Trp His Pro Leu Asn Xaa Cys
1               5                   10

<210> SEQ ID NO 6
<211> LENGTH: 13
<212> TYPE: PRT
<213> ORGANISM: Artificial
<220> FEATURE:
<223> OTHER INFORMATION: Synthetic Peptide

<400> SEQUENCE: 6

Cys Leu Tyr Ser Pro Cys Trp His Pro Leu Asn Asp Cys
1               5                   10

<210> SEQ ID NO 7
<211> LENGTH: 13
<212> TYPE: PRT
<213> ORGANISM: Artificial
<220> FEATURE:
<223> OTHER INFORMATION: Synthetic Peptide

<400> SEQUENCE: 7

Cys Asn Tyr Ser Pro Cys Trp His Pro Leu Asn Lys Cys
1               5                   10

```
<210> SEQ ID NO 8
<211> LENGTH: 13
<212> TYPE: PRT
<213> ORGANISM: Artificial
<220> FEATURE:
<223> OTHER INFORMATION: Synthetic Peptide

<400> SEQUENCE: 8

Cys Trp Tyr Glu Tyr Asp Cys Asn Asn Trp Glu Arg Cys
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic Peptide

<400> SEQUENCE: 9

Cys Val Ile Arg Tyr Ser Pro Cys Ser His Tyr Leu Asn Cys
1               5                   10

<210> SEQ ID NO 10
<211> LENGTH: 14
<212> TYPE: PRT
<213> ORGANISM: Artificial
<220> FEATURE:
<223> OTHER INFORMATION: Synthetic Peptide

<400> SEQUENCE: 10

Cys Asp Tyr Ser Pro Trp Trp His Pro Cys Asn His Ile Cys
1               5                   10

<210> SEQ ID NO 11
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 11

Cys Pro Xaa Asp Cys Met Xaa Asp Trp Ser Thr Pro Xaa Trp Cys
1               5                   10                  15

<210> SEQ ID NO 12
<211> LENGTH: 12
<212> TYPE: PRT
<213> ORGANISM: Artificial
<220> FEATURE:
<223> OTHER INFORMATION: Synthetic Peptide

<400> SEQUENCE: 12

Cys Asp Ala Cys Leu Tyr Pro Asp Tyr Tyr Val Cys
1               5                   10

<210> SEQ ID NO 13
```

```
<211> LENGTH: 13
<212> TYPE: PRT
<213> ORGANISM: Artificial
<220> FEATURE:
<223> OTHER INFORMATION: Synthetic Peptide

<400> SEQUENCE: 13

Cys Arg Leu Trp Cys Ile Pro Ala Pro Thr Asp Asp Cys
1               5                   10

<210> SEQ ID NO 14
<211> LENGTH: 13
<212> TYPE: PRT
<213> ORGANISM: Artificial
<220> FEATURE:
<223> OTHER INFORMATION: Synthetic Peptide

<400> SEQUENCE: 14

Cys Thr Met Trp Cys Ile Pro Ala Lys Gly Asp Trp Cys
1               5                   10

<210> SEQ ID NO 15
<211> LENGTH: 13
<212> TYPE: PRT
<213> ORGANISM: Artificial
<220> FEATURE:
<223> OTHER INFORMATION: Synthetic Peptide

<400> SEQUENCE: 15

Cys Met Leu Trp Cys Leu Pro Ala Pro Thr Asp Glu Cys
1               5                   10

<210> SEQ ID NO 16
<211> LENGTH: 13
<212> TYPE: PRT
<213> ORGANISM: Artificial
<220> FEATURE:
<223> OTHER INFORMATION: Synthetic Peptide

<400> SEQUENCE: 16

Cys Ile Leu Trp Cys Leu Pro Glu Pro Pro Asp Glu Cys
1               5                   10

<210> SEQ ID NO 17
<211> LENGTH: 13
<212> TYPE: PRT
<213> ORGANISM: Artificial
<220> FEATURE:
<223> OTHER INFORMATION: Synthetic Peptide

<400> SEQUENCE: 17

Cys Leu Leu Trp Cys Ile Pro Asn Pro Asp Asp Asn Cys
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic Peptide

<400> SEQUENCE: 18

Cys Trp Leu Trp Cys Val Pro Asn Pro Asp Asp Thr Cys
1               5                   10

<210> SEQ ID NO 19
<211> LENGTH: 13
```

<212> TYPE: PRT
<213> ORGANISM: Artificial
<220> FEATURE:
<223> OTHER INFORMATION: Synthetic Peptide

<400> SEQUENCE: 19

Cys Val Leu Trp Cys Thr Pro Tyr Pro Gly Asp Asp Cys
1               5                   10

<210> SEQ ID NO 20
<211> LENGTH: 13
<212> TYPE: PRT
<213> ORGANISM: Artificial
<220> FEATURE:
<223> OTHER INFORMATION: Synthetic Peptide

<400> SEQUENCE: 20

Cys Ala Leu Trp Cys Ile Pro Asp Pro Gln Asp Glu Cys
1               5                   10

<210> SEQ ID NO 21
<211> LENGTH: 13
<212> TYPE: PRT
<213> ORGANISM: Artificial
<220> FEATURE:
<223> OTHER INFORMATION: Synthetic Peptide

<400> SEQUENCE: 21

Cys Thr Leu Trp Cys Ile Pro Asp Ala Ser Asp Ser Cys
1               5                   10

<210> SEQ ID NO 22
<211> LENGTH: 13
<212> TYPE: PRT
<213> ORGANISM: Artificial
<220> FEATURE:
<223> OTHER INFORMATION: Synthetic Peptide

<400> SEQUENCE: 22

Cys Gln Leu Trp Cys Ile Pro Asp Ala Asp Asp Asp Cys
1               5                   10

<210> SEQ ID NO 23
<211> LENGTH: 13
<212> TYPE: PRT
<213> ORGANISM: Artificial
<220> FEATURE:
<223> OTHER INFORMATION: Synthetic Peptide

<400> SEQUENCE: 23

Cys Gln Leu Trp Cys Val Pro Glu Pro Gly Asp Ser Cys
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic Peptide

<400> SEQUENCE: 24

Cys Ala Leu Trp Cys Ile Pro Glu Glu Ser Asp Asp Cys
1               5                   10

<210> SEQ ID NO 25
<211> LENGTH: 13
<212> TYPE: PRT

```
<213> ORGANISM: Artificial
<220> FEATURE:
<223> OTHER INFORMATION: Synthetic Peptide

<400> SEQUENCE: 25

Cys Val Leu Trp Cys Ile Pro Glu Pro Gln Asp Lys Cys
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic Peptide

<400> SEQUENCE: 26

Cys Thr Leu Trp Cys Ile Pro Asp Pro Asp Asp Ser Cys
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic Peptide

<400> SEQUENCE: 27

Cys Arg Leu Trp Cys Val Pro Lys Ala Glu Asp Tyr Cys
1               5                   10

<210> SEQ ID NO 28
<211> LENGTH: 13
<212> TYPE: PRT
<213> ORGANISM: Artificial
<220> FEATURE:
<223> OTHER INFORMATION: Synthetic Peptide

<400> SEQUENCE: 28

Cys Thr Lys Pro Cys Ile Ala Tyr Tyr Asn Gln Ser Cys
1               5                   10

<210> SEQ ID NO 29
<211> LENGTH: 13
<212> TYPE: PRT
<213> ORGANISM: Artificial
<220> FEATURE:
<223> OTHER INFORMATION: Synthetic Peptide

<400> SEQUENCE: 29

Cys Met Asn Pro Cys Ile Ala Tyr Tyr Gln Gln Glu Cys
1               5                   10

<210> SEQ ID NO 30
<211> LENGTH: 13
<212> TYPE: PRT
<213> ORGANISM: Artificial
<220> FEATURE:
<223> OTHER INFORMATION: Synthetic Peptide

<400> SEQUENCE: 30

Cys Thr Asn Ala Cys Val Ala Tyr Tyr His Gln Ala Cys
1               5                   10

<210> SEQ ID NO 31
<211> LENGTH: 13
<212> TYPE: PRT
<213> ORGANISM: Artificial
```

```
<220> FEATURE:
<223> OTHER INFORMATION: Synthetic Peptide

<400> SEQUENCE: 31

Cys Ser Asp Pro Cys Ile Ser Tyr Tyr Asn Gln Ala Cys
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic Peptide

<400> SEQUENCE: 32

Cys Asp Pro Pro Cys Asp Pro Phe Trp Tyr Ala Phe Tyr Cys
1               5                   10

<210> SEQ ID NO 33
<211> LENGTH: 14
<212> TYPE: PRT
<213> ORGANISM: Artificial
<220> FEATURE:
<223> OTHER INFORMATION: Synthetic Peptide

<400> SEQUENCE: 33

Cys Pro Asp Asp Cys Asp Pro Phe Trp Tyr Asn Phe Tyr Cys
1               5                   10

<210> SEQ ID NO 34
<211> LENGTH: 12
<212> TYPE: PRT
<213> ORGANISM: Artificial
<220> FEATURE:
<223> OTHER INFORMATION: Synthetic Peptide

<400> SEQUENCE: 34

Cys Arg Tyr Ser Pro Cys Tyr His Pro His Asn Cys
1               5                   10

<210> SEQ ID NO 35
<211> LENGTH: 13
<212> TYPE: PRT
<213> ORGANISM: Artificial
<220> FEATURE:
<223> OTHER INFORMATION: Synthetic Peptide

<400> SEQUENCE: 35

Cys Leu Tyr Ser Pro Cys Asn His Pro Leu Asn Ser Cys
1               5                   10

<210> SEQ ID NO 36
<211> LENGTH: 13
<212> TYPE: PRT
<213> ORGANISM: Artificial
<220> FEATURE:
<223> OTHER INFORMATION: Synthetic Peptide

<400> SEQUENCE: 36

Cys Glu Asp Asn Tyr Cys Phe Met Trp Thr Pro Tyr Cys
1               5                   10

<210> SEQ ID NO 37
<211> LENGTH: 13
<212> TYPE: PRT
<213> ORGANISM: Artificial
<220> FEATURE:
```

```
<223> OTHER INFORMATION: Synthetic Peptide

<400> SEQUENCE: 37

Cys Leu Asp Ser Pro Cys Trp His Pro Leu Asn Asp Cys
1               5                   10

<210> SEQ ID NO 38
<211> LENGTH: 13
<212> TYPE: PRT
<213> ORGANISM: Artificial
<220> FEATURE:
<223> OTHER INFORMATION: Synthetic Peptide

<400> SEQUENCE: 38

Cys Arg Phe Ser Pro Cys Ser His Pro Leu Asn Gln Cys
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic Peptide

<400> SEQUENCE: 39

Cys Lys Tyr Ser Pro Cys Trp His Pro Leu Asn Leu Cys
1               5                   10

<210> SEQ ID NO 40
<211> LENGTH: 13
<212> TYPE: PRT
<213> ORGANISM: Artificial
<220> FEATURE:
<223> OTHER INFORMATION: Synthetic Peptide

<400> SEQUENCE: 40

Cys Arg Tyr Ser Pro Cys Trp His Pro Leu Asn Asn Cys
1               5                   10

<210> SEQ ID NO 41
<211> LENGTH: 15
<212> TYPE: PRT
<213> ORGANISM: Artificial
<220> FEATURE:
<223> OTHER INFORMATION: Synthetic Peptide

<400> SEQUENCE: 41

Cys Glu Trp Ile Ser Cys Pro Gly Glu Pro His Arg Trp Trp Cys
1               5                   10                  15

<210> SEQ ID NO 42
<211> LENGTH: 15
<212> TYPE: PRT
<213> ORGANISM: Artificial
<220> FEATURE:
<223> OTHER INFORMATION: Synthetic Peptide

<400> SEQUENCE: 42

Cys Val Trp Glu Ala Cys Pro Glu His Pro Asp Gln Trp Trp Cys
1               5                   10                  15

<210> SEQ ID NO 43
<211> LENGTH: 15
<212> TYPE: PRT
<213> ORGANISM: Artificial
<220> FEATURE:
<223> OTHER INFORMATION: Synthetic Peptide
```

<400> SEQUENCE: 43

Cys Ser Thr Trp His Cys Phe Trp Asn Leu Gln Glu Gly Lys Cys
1               5                   10                  15

<210> SEQ ID NO 44
<211> LENGTH: 15
<212> TYPE: PRT
<213> ORGANISM: Artificial
<220> FEATURE:
<223> OTHER INFORMATION: Synthetic Peptide

<400> SEQUENCE: 44

Cys Glu Trp Lys Ala Cys Glu His Asp Arg Glu Arg Trp Trp Cys
1               5                   10                  15

<210> SEQ ID NO 45
<211> LENGTH: 15
<212> TYPE: PRT
<213> ORGANISM: Artificial
<220> FEATURE:
<223> OTHER INFORMATION: Synthetic Peptide

<400> SEQUENCE: 45

Cys Arg Thr Trp Gln Cys Phe Tyr Glu Trp Gln Asn Gly His Cys
1               5                   10                  15

<210> SEQ ID NO 46
<211> LENGTH: 15
<212> TYPE: PRT
<213> ORGANISM: Artificial
<220> FEATURE:
<223> OTHER INFORMATION: Synthetic Peptide

<400> SEQUENCE: 46

Cys Lys Thr Trp Asp Cys Phe Trp Ala Ser Gln Val Ser Glu Cys
1               5                   10                  15

<210> SEQ ID NO 47
<211> LENGTH: 15
<212> TYPE: PRT
<213> ORGANISM: Artificial
<220> FEATURE:
<223> OTHER INFORMATION: Synthetic Peptide

<400> SEQUENCE: 47

Cys Ser Thr Trp Gln Cys Phe Tyr Asp Leu Gln Glu Gly His Cys
1               5                   10                  15

<210> SEQ ID NO 48
<211> LENGTH: 15
<212> TYPE: PRT
<213> ORGANISM: Artificial
<220> FEATURE:
<223> OTHER INFORMATION: Synthetic Peptide

<400> SEQUENCE: 48

Cys Thr Thr Trp Glu Cys Phe Tyr Asp Leu Gln Glu Gly His Cys
1               5                   10                  15

<210> SEQ ID NO 49
<211> LENGTH: 15
<212> TYPE: PRT
<213> ORGANISM: Artificial
<220> FEATURE:
<223> OTHER INFORMATION: Synthetic Peptide

```
<400> SEQUENCE: 49

Cys Glu Thr Trp Glu Cys Phe Trp Arg Leu Gln Ala Gly Glu Cys
1               5                   10                  15

<210> SEQ ID NO 50
<211> LENGTH: 15
<212> TYPE: PRT
<213> ORGANISM: Artificial
<220> FEATURE:
<223> OTHER INFORMATION: Synthetic Peptide

<400> SEQUENCE: 50

Cys Arg Thr Trp Gln Cys Phe Trp Asp Leu Gln Glu Gly Leu Cys
1               5                   10                  15

<210> SEQ ID NO 51
<211> LENGTH: 15
<212> TYPE: PRT
<213> ORGANISM: Artificial
<220> FEATURE:
<223> OTHER INFORMATION: Synthetic Peptide

<400> SEQUENCE: 51

Cys Ser Thr Trp Gln Cys Phe Trp Asp Ser Gln Leu Gly Ala Cys
1               5                   10                  15

<210> SEQ ID NO 52
<211> LENGTH: 15
<212> TYPE: PRT
<213> ORGANISM: Artificial
<220> FEATURE:
<223> OTHER INFORMATION: Synthetic Peptide

<400> SEQUENCE: 52

Cys Glu Thr Trp Glu Cys Phe Trp Glu Trp Gln Val Gly Ser Cys
1               5                   10                  15

<210> SEQ ID NO 53
<211> LENGTH: 15
<212> TYPE: PRT
<213> ORGANISM: Artificial
<220> FEATURE:
<223> OTHER INFORMATION: Synthetic Peptide

<400> SEQUENCE: 53

Cys Thr Thr Trp Glu Cys Phe Trp Asp Leu Gln Glu Gly Leu Cys
1               5                   10                  15

<210> SEQ ID NO 54
<211> LENGTH: 15
<212> TYPE: PRT
<213> ORGANISM: Artificial
<220> FEATURE:
<223> OTHER INFORMATION: Synthetic Peptide

<400> SEQUENCE: 54

Cys His Thr Trp Asp Cys Phe Tyr Gln Trp Gln Asp Gly His Cys
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic Peptide
```

```
<400> SEQUENCE: 55

Cys Thr Thr Trp Glu Cys Phe Tyr Ser Leu Gln Asp Gly His Cys
1               5                   10                  15

<210> SEQ ID NO 56
<211> LENGTH: 13
<212> TYPE: PRT
<213> ORGANISM: Artificial
<220> FEATURE:
<223> OTHER INFORMATION: Synthetic Peptide

<400> SEQUENCE: 56

Cys Asn Glu Asp Met Tyr Cys Phe Met Trp Met Glu Cys
1               5                   10

<210> SEQ ID NO 57
<211> LENGTH: 13
<212> TYPE: PRT
<213> ORGANISM: Artificial
<220> FEATURE:
<223> OTHER INFORMATION: Synthetic Peptide

<400> SEQUENCE: 57

Cys Leu Tyr Glu Tyr Asp Cys Tyr Thr Trp Arg Arg Cys
1               5                   10

<210> SEQ ID NO 58
<211> LENGTH: 13
<212> TYPE: PRT
<213> ORGANISM: Artificial
<220> FEATURE:
<223> OTHER INFORMATION: Synthetic Peptide

<400> SEQUENCE: 58

Cys Arg Tyr Glu Tyr Asp Cys His Thr Trp Gln Arg Cys
1               5                   10

<210> SEQ ID NO 59
<211> LENGTH: 13
<212> TYPE: PRT
<213> ORGANISM: Artificial
<220> FEATURE:
<223> OTHER INFORMATION: Synthetic Peptide

<400> SEQUENCE: 59

Cys Trp Tyr Glu Tyr Asp Cys Thr Thr Trp Glu Arg Cys
1               5                   10

<210> SEQ ID NO 60
<211> LENGTH: 13
<212> TYPE: PRT
<213> ORGANISM: Artificial
<220> FEATURE:
<223> OTHER INFORMATION: Synthetic Peptide

<400> SEQUENCE: 60

Cys Trp Tyr Glu Tyr Asp Cys Arg Thr Trp Thr Arg Cys
1               5                   10

<210> SEQ ID NO 61
<211> LENGTH: 13
<212> TYPE: PRT
<213> ORGANISM: Artificial
<220> FEATURE:
<223> OTHER INFORMATION: Synthetic Peptide
```

<400> SEQUENCE: 61

Cys Leu Tyr Glu Tyr Asp Cys His Thr Trp Thr Arg Cys
1               5                   10

<210> SEQ ID NO 62
<211> LENGTH: 13
<212> TYPE: PRT
<213> ORGANISM: Artificial
<220> FEATURE:
<223> OTHER INFORMATION: Synthetic Peptide

<400> SEQUENCE: 62

Cys Trp Tyr Glu Tyr Asp Cys Arg Thr Trp Thr Phe Cys
1               5                   10

<210> SEQ ID NO 63
<211> LENGTH: 15
<212> TYPE: PRT
<213> ORGANISM: Artificial
<220> FEATURE:
<223> OTHER INFORMATION: Synthetic Peptide

<400> SEQUENCE: 63

Cys His Gly Gly Val Trp Cys Ile Pro Asn Ile Asn Asp Ser Cys
1               5                   10                  15

<210> SEQ ID NO 64
<211> LENGTH: 15
<212> TYPE: PRT
<213> ORGANISM: Artificial
<220> FEATURE:
<223> OTHER INFORMATION: Synthetic Peptide

<400> SEQUENCE: 64

Cys Asp Ser Pro Val Arg Cys Tyr Trp Asn Thr Gln Lys Gly Cys
1               5                   10                  15

<210> SEQ ID NO 65
<211> LENGTH: 15
<212> TYPE: PRT
<213> ORGANISM: Artificial
<220> FEATURE:
<223> OTHER INFORMATION: Synthetic Peptide

<400> SEQUENCE: 65

Cys Gly Ser Pro Val Pro Cys Tyr Trp Asn Thr Arg Lys Gly Cys
1               5                   10                  15

<210> SEQ ID NO 66
<211> LENGTH: 14
<212> TYPE: PRT
<213> ORGANISM: Artificial
<220> FEATURE:
<223> OTHER INFORMATION: Synthetic Peptide

<400> SEQUENCE: 66

Cys Ala Pro Phe Glu Phe Asn Cys Tyr Thr Trp Arg Pro Cys
1               5                   10

<210> SEQ ID NO 67
<211> LENGTH: 14
<212> TYPE: PRT
<213> ORGANISM: Artificial
<220> FEATURE:
<223> OTHER INFORMATION: Synthetic Peptide

<400> SEQUENCE: 67

Cys Arg Val Leu Tyr Ser Pro Cys Tyr His Trp Leu Asn Cys
1               5                   10

<210> SEQ ID NO 68
<211> LENGTH: 15
<212> TYPE: PRT
<213> ORGANISM: Artificial
<220> FEATURE:
<223> OTHER INFORMATION: Synthetic Peptide

<400> SEQUENCE: 68

Cys Ser Ile Met Tyr Ser Pro Cys Glu His Pro His Asn His Cys
1               5                   10                  15

<210> SEQ ID NO 69
<211> LENGTH: 14
<212> TYPE: PRT
<213> ORGANISM: Artificial
<220> FEATURE:
<223> OTHER INFORMATION: Synthetic Peptide

<400> SEQUENCE: 69

Cys Asp Lys Trp Glu Pro Asp His Leu Cys Tyr Trp Trp Cys
1               5                   10

<210> SEQ ID NO 70
<211> LENGTH: 14
<212> TYPE: PRT
<213> ORGANISM: Artificial
<220> FEATURE:
<223> OTHER INFORMATION: Synthetic Peptide

<400> SEQUENCE: 70

Cys Asp Ala Trp Pro Glu Thr His Val Cys Tyr Trp Trp Cys
1               5                   10

<210> SEQ ID NO 71
<211> LENGTH: 14
<212> TYPE: PRT
<213> ORGANISM: Artificial
<220> FEATURE:
<223> OTHER INFORMATION: Synthetic Peptide

<400> SEQUENCE: 71

Cys Asp Glu Tyr Thr Pro Glu His Leu Cys Tyr Trp Trp Cys
1               5                   10

<210> SEQ ID NO 72
<211> LENGTH: 15
<212> TYPE: PRT
<213> ORGANISM: Artificial
<220> FEATURE:
<223> OTHER INFORMATION: Synthetic Peptide

<400> SEQUENCE: 72

Cys Trp Ile Asn Tyr Ser Ile Ser Pro Cys Tyr Val Gly Glu Cys
1               5                   10                  15

<210> SEQ ID NO 73
<211> LENGTH: 15
<212> TYPE: PRT
<213> ORGANISM: Artificial
<220> FEATURE:
<223> OTHER INFORMATION: Synthetic Peptide

```
<400> SEQUENCE: 73

Cys Arg Tyr Glu Tyr Pro Glu His Leu Cys Tyr Thr Trp Gln Cys
1               5                   10                  15
```

BICYCLIC PEPTIDE LIGANDS SPECIFIC FOR OX40

CROSS-REFERENCE TO RELATED APPLICATIONS

This application claims priority under 35 U.S.C. § 119 to U.S. Provisional Application No. 62/845,473, filed May 9, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 23, 2022, is named Bicycle 174055 SL.txt and is 16.3 kilobytes in size.

FIELD OF THE INVENTION

The present invention relates to polypeptides which are covalently bound to molecular scaffolds such that two or more peptide loops are subtended between attachment points to the scaffold. In particular, the invention describes peptides which bind to OX40. The invention also relates to multimeric binding complexes of polypeptides which are covalently bound to molecular scaffolds such that two or more peptide loops are subtended between attachment points to the scaffold that are functional agonists of OX40. The invention also includes drug conjugates comprising said peptides and complexes, conjugated to one or more effector and/or functional groups, to pharmaceutical compositions comprising said peptide ligands, complexes and drug conjugates and to the use of said peptide ligands and drug conjugates in preventing, suppressing or treating a disease or disorder mediated by OX40.

BACKGROUND OF THE INVENTION

Cyclic peptides are able to bind with high affinity and specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296 (5565), 151-5) or the cyclic peptide inhibitor upain-1 binding to urokinase-type plasminogen activator (603 $Å^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) (Heinis et al (2014) Angewandte Chemie, International Edition 53(6) 1602-1606).

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-$(Xaa)_6$-Cys-$(Xaa)_6$-Cys) were displayed on phage and cyclised by covalently linking the cysteine side chains to a small molecule scaffold.

SUMMARY OF THE INVENTION

According to a first aspect of the invention, there is provided a peptide ligand specific for OX40 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a multimeric binding complex which comprises at least two peptide ligands, wherein at least one peptide ligand is specific for OX40 as defined herein and said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a yet further aspect of the invention, there is provided a drug conjugate comprising the peptide ligand or multimeric binding complex as defined herein, conjugated to one or more effector and/or functional groups.

According to a yet further aspect of the invention, there is provided a pharmaceutical composition comprising a peptide ligand, multimeric binding complex or drug conjugate as defined herein in combination with one or more pharmaceutically acceptable excipients.

According to a further aspect of the invention, there is provided a peptide ligand, multimeric binding complex, drug conjugate or pharmaceutical composition as defined herein for use in preventing, suppressing or treating a disease or disorder mediated by OX40.

DETAILED DESCRIPTION OF THE INVENTION

Peptide Ligands

Figure 1:
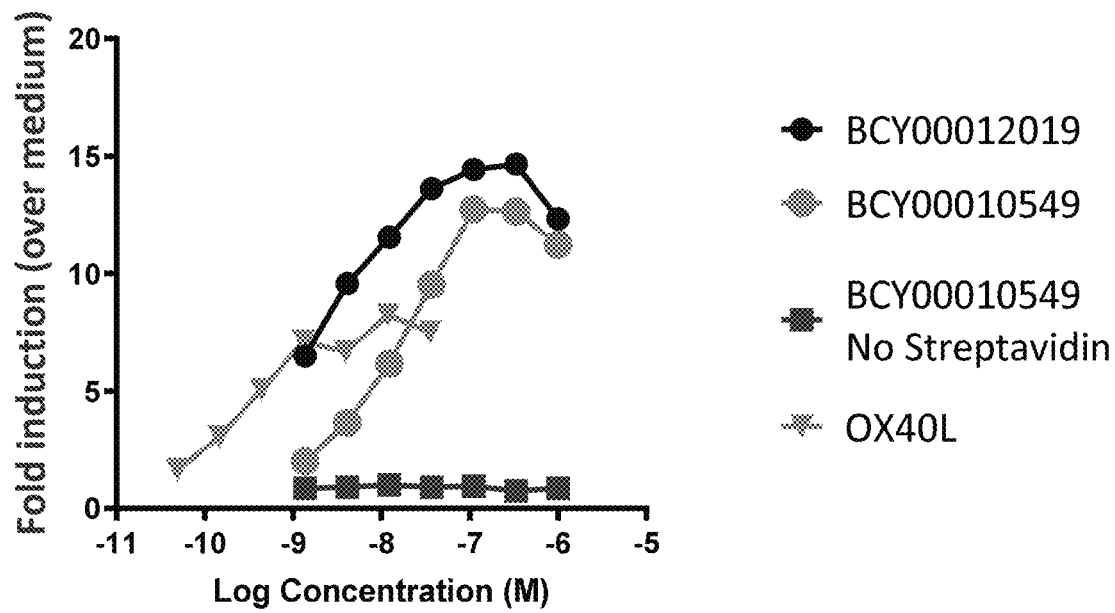
FIG. 1: Results of OX40L, BCY10549 (biotinylated monomer), BCY10549+Streptavidin and BCY12019 (tetramer) tested in Promega's OX40 reporter cell assay.

According to a first aspect of the invention, there is provided a peptide ligand specific for OX40 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

In one embodiment, said reactive groups comprise cysteine residues.

In a further embodiment, said loop sequences comprise 2, 3, 4, 5, 6, 7 or 8 amino acids.

In a yet further embodiment, said loop sequences comprise 3, 4, 5, 6, 7 or 8 amino acids.

In one embodiment, said loop sequences comprise three cysteine residues separated by two loop sequences the first of which consists of 2 amino acids and the second of which consists of 7 amino acids.

In one embodiment, said loop sequences comprise three cysteine residues separated by two loop sequences the first of which consists of 3 amino acids and the second of which consists of 7 amino acids.

In one embodiment, said loop sequences comprise three cysteine residues separated by two loop sequences the first of which consists of 3 amino acids and the second of which consists of 8 amino acids.

In one embodiment, said loop sequences comprise three cysteine residues separated by two loop sequences the first of which consists of 4 amino acids and the second of which consists of 5 amino acids.

In one embodiment, said loop sequences comprise three cysteine residues separated by two loop sequences the first of which consists of 4 amino acids and the second of which consists of 6 amino acids.

In one embodiment, said loop sequences comprise three cysteine residues separated by two loop sequences the first of which consists of 4 amino acids and the second of which consists of 8 amino acids.

In one embodiment, said loop sequences comprise three cysteine residues separated by two loop sequences both of which consist of 5 amino acids.

In one embodiment, said loop sequences comprise three cysteine residues separated by two loop sequences the first of which consists of 5 amino acids and the second of which consists of 7 amino acids.

In one embodiment, said loop sequences comprise three cysteine residues separated by two loop sequences the first of which consists of 6 amino acids and the second of which consists of 5 amino acids.

In one embodiment, said loop sequences comprise three cysteine residues separated by two loop sequences both of which consist of 6 amino acids.

In one embodiment, said loop sequences comprise three cysteine residues separated by two loop sequences the first of which consists of 8 amino acids and the second of which consists of 3 amino acids.

In one embodiment, said loop sequences comprise three cysteine residues separated by two loop sequences the first of which consists of 8 amino acids and the second of which consists of 4 amino acids.

In one embodiment, said loop sequences comprise three cysteine residues separated by two loop sequences, the first of which comprises 2 amino acids and the second of which comprises 7 amino acids and the amino acid sequence comprises:

$C_i$DAC$_{ii}$LYPDYYVC$_{iii}$; (SEQ ID NO: 12)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than SEQ ID NO: 12.

In a further embodiment, said loop sequences comprise three cysteine residues separated by two loop sequences, the first of which comprises 2 amino acids and the second of which comprises 7 amino acids and the amino acid sequence has N- and/or C-terminal modifications and comprises:

A-(SEQ ID NO: 12)-A (herein referred to as BCY10375).

In one embodiment, said loop sequences comprise three cysteine residues separated by two loop sequences, the first of which comprises 3 amino acids and the second of which comprises 7 amino acids and the amino acid sequence comprises:

$C_i$RLWC$_{ii}$IPAPTDDC$_{iii}$; (SEQ ID NO: 13)

$C_i$TMWC$_{ii}$IPAKGDWC$_{iii}$; (SEQ ID NO: 14)

$C_i$MLWC$_{ii}$LPAPTDEC$_{iii}$; (SEQ ID NO: 15)

$C_i$ILWC$_{ii}$LPEPPDEC$_{iii}$; (SEQ ID NO: 16)

$C_i$LLWC$_{ii}$IPNPDDNC$_{iii}$; (SEQ ID NO: 17)

$C_i$WLWC$_{ii}$VPNPDDTC$_{iii}$; (SEQ ID NO: 18)

$C_i$VLWC$_{ii}$TPYPGDDC$_{iii}$; (SEQ ID NO: 19)

$C_i$ALWC$_{ii}$IPDPQDEC$_{iii}$; (SEQ ID NO: 20)

$C_i$TLWC$_{ii}$IPDASDSC$_{iii}$; (SEQ ID NO: 21)

$C_i$QLWC$_{ii}$IPDADDDC$_{iii}$; (SEQ ID NO: 22)

$C_i$QLWC$_{ii}$VPEPGDSC$_{iii}$; (SEQ ID NO: 23)

$C_i$ALWC$_{ii}$IPEESDDC$_{iii}$; (SEQ ID NO: 24)

$C_i$YLWC$_{ii}$IPEPQDKC$_{iii}$; (SEQ ID NO: 25)

$C_i$TLWC$_{ii}$IPDPDDSC$_{iii}$; (SEQ ID NO: 26)

-continued $C_iRLWC_{ii}VPKAEDYC_{iii}$; (SEQ ID NO: 27)

$C_iTKPC_{ii}IAYYNQSC_{iii}$; (SEQ ID NO: 28)

$C_iMNPC_{ii}IAYYQQEC_{iii}$; (SEQ ID NO: 29)

$C_iTNAC_{ii}VAYYHQAC_{iii}$; and (SEQ ID NO: 30)

$C_iSDPC_{ii}ISYYNQAC_{iii}$; (SEQ ID NO: 31)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than any one or more or all of SEQ ID NOS: 13-31.

In a further embodiment, said loop sequences comprise three cysteine residues separated by two loop sequences, the first of which comprises 3 amino acids and the second of which comprises 7 amino acids and the amino acid sequence has N- and/or C-terminal modifications and comprises:
- A-(SEQ ID NO: 13)-A (herein referred to as BCY10364);
- A-(SEQ ID NO: 14)-A (herein referred to as BCY10365);
- A-(SEQ ID NO: 15)-A (herein referred to as BCY10366);
- A-(SEQ ID NO: 16)-A (herein referred to as BCY10367);
- A-(SEQ ID NO: 17)-A (herein referred to as BCY10368);
- A-(SEQ ID NO: 18)-A (herein referred to as BCY10369);
- A-(SEQ ID NO: 19)-A (herein referred to as BCY10374);
- A-(SEQ ID NO: 20)-A (herein referred to as BCY10376);
- A-(SEQ ID NO: 21)-A (herein referred to as BCY10737);
- A-(SEQ ID NO: 22)-A (herein referred to as BCY10738);
- A-(SEQ ID NO: 23)-A (herein referred to as BCY10739);
- A-(SEQ ID NO: 24)-A (herein referred to as BCY10740);
- A-(SEQ ID NO: 25)-A (herein referred to as BCY10741);
- A-(SEQ ID NO: 26)-A (herein referred to as BCY10742);
- A-(SEQ ID NO: 27)-A (herein referred to as BCY10380);
- A-(SEQ ID NO: 28)-A (herein referred to as BCY10370);
- A-(SEQ ID NO: 29)-A (herein referred to as BCY10372);
- A-(SEQ ID NO: 30)-A (herein referred to as BCY10373); and
- A-(SEQ ID NO: 31)-A (herein referred to as BCY10379).

In an alternative embodiment, said loop sequences comprise three cysteine residues separated by two loop sequences, the first of which comprises 3 amino acids and the second of which comprises 7 amino acids and the amino acid sequence comprises:

$C_iILWC_{ii}LPEPHDEC_{iii}$, (SEQ ID NO: 1)

wherein $C_i$, $C_{ii}$ and $C_{iii}$ represent first, second and third cysteine residues, respectively, or a modified derivative, or a pharmaceutically acceptable salt thereof.

In a further embodiment, said loop sequences comprise three cysteine residues separated by two loop sequences, the first of which comprises 3 amino acids and the second of which comprises 7 amino acids and the amino acid sequence has N- and/or C-terminal modifications and comprises:
- A-(SEQ ID NO: 1)-A-[Sar6]-[KBiot] (herein referred to as BCY10551); and
- A-(SEQ ID NO: 1)-A (herein referred to as BCY10371), such as:
- A-(SEQ ID NO: 1)-A-[Sar6]-[KBiot] (herein referred to as BCY10551).

In one embodiment, said loop sequences comprise three cysteine residues separated by two loop sequences, the first of which comprises 3 amino acids and the second of which comprises 8 amino acids and the amino acid sequence comprises:

$C_iDPPCHDPFWYAFYC_{iii}$; and (SEQ ID NO: 32)

$C_iPDDCHDPFWYNFYC_{iii}$; (SEQ ID NO: 33)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than either of or both of SEQ ID NOS: 32-33.

In a further embodiment, said loop sequences comprise three cysteine residues separated by two loop sequences, the first of which comprises 3 amino acids and the second of which comprises 8 amino acids and the amino acid sequence has N- and/or C-terminal modifications and comprises:
- A-(SEQ ID NO: 32)-A (herein referred to as BCY10377); and
- A-(SEQ ID NO: 33)-A (herein referred to as BCY10744).

In an alternative embodiment, said loop sequences comprise three cysteine residues separated by two loop sequences, the first of which comprises 3 amino acids and the second of which comprises 8 amino acids and the amino acid sequence comprises:

$C_iA^K/_S{}^N/_E C_{ii}DPFWYQFYC_{iii}$, (SEQ ID NO: 2)

wherein $C_i$, $C_{ii}$ and $C_{iii}$ represent first, second and third cysteine residues, respectively, or a modified derivative, or a pharmaceutically acceptable salt thereof.

In a further embodiment, the peptide ligand of $C_iA^K/_S{}^N/_E C_{ii}DPFWYQFYC_{iii}$ (SEQ ID NO: 2) comprises an amino acid sequence selected from:

$C_iAKNC_{ii}DPFWYQFYC_{iii}$, (SEQ ID NO: 3) and $C_iASEC_{ii}DPFWYQFYC_{iii}$; (SEQ ID NO: 4)

wherein $C_i$, $C_{ii}$ and $C_{iii}$ represent first, second and third cysteine residues, respectively, or a modified derivative, or a pharmaceutically acceptable salt thereof.

In a yet further embodiment, said loop sequences comprise three cysteine residues separated by two loop sequences, the first of which comprises 3 amino acids and the second of which comprises 8 amino acids and the amino acid sequence has N- and/or C-terminal modifications and comprises:
- A-(SEQ ID NO: 3)-A-[Sar6]-[KBiot] (herein referred to as BCY10552);
- [Biot]-G-[Sar5]-A-(SEQ ID NO: 3)-A (herein referred to as BCY10479);
- A-(SEQ ID NO: 3)-A (herein referred to as BCY10378);

[Biot]-G-[Sar5]-A-(SEQ ID NO: 4)-A (herein referred to as BCY11371); and
A-(SEQ ID NO: 4)-A (herein referred to as BCY10743), such as:
A-(SEQ ID NO: 3)-A-[Sar6]-[KBiot] (herein referred to as BCY10552);
[Biot]-G-[Sar5]-A-(SEQ ID NO: 3)-A (herein referred to as BCY10479); and
[Biot]-G-[Sar5]-A-(SEQ ID NO: 4)-A (herein referred to as BCY11371).

In one embodiment, said loop sequences comprise three cysteine residues separated by two loop sequences, the first of which comprises 4 amino acids and the second of which comprises 5 amino acids and the amino acid sequence comprises:

$C_i$RYSPC$_{ii}$YHPHNC$_{iii}$; (SEQ ID NO: 34)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than SEQ ID NO: 34.

In a further embodiment, said loop sequences comprise three cysteine residues separated by two loop sequences, the first of which comprises 4 amino acids and the second of which comprises 5 amino acids and the amino acid sequence has N- and/or C-terminal modifications and comprises:
A-(SEQ ID NO: 34)-A (herein referred to as BCY10343).

In one embodiment, said loop sequences comprise three cysteine residues separated by two loop sequences, the first of which comprises 4 amino acids and the second of which comprises 6 amino acids and the amino acid sequence comprises:

$C_i$LYSPC$_{ii}$NHPLNSC$_{iii}$; (SEQ ID NO: 35)

$C_i$EDNYC$_{ii}$FMWTPYC$_{iii}$; (SEQ ID NO: 36)

$C_i$LDSPC$_{ii}$WHPLNDC$_{iii}$; (SEQ ID NO: 37)

$C_i$RFSPC$_{ii}$SHPLNQC$_{iii}$; (SEQ ID NO: 38)

$C_i$KYSPC$_{ii}$WHPLNLC$_{iii}$; and (SEQ ID NO: 39)

$C_i$RYSPC$_{ii}$WHPLNNC$_i$; (SEQ ID NO: 40)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than one or more or all of SEQ ID NOS: 35-40.

In a further embodiment, said loop sequences comprise three cysteine residues separated by two loop sequences, the first of which comprises 4 amino acids and the second of which comprises 6 amino acids and the amino acid sequence has N- and/or C-terminal modifications and comprises:
A-(SEQ ID NO: 35)-A (herein referred to as BCY10350);
A-(SEQ ID NO: 36)-A (herein referred to as BCY10352);
A-(SEQ ID NO: 37)-A (herein referred to as BCY10353);
A-(SEQ ID NO: 38)-A (herein referred to as BCY10354);
A-(SEQ ID NO: 39)-A (herein referred to as BCY10730); and
A-(SEQ ID NO: 40)-A (herein referred to as BCY10731).

In an alternative embodiment, said loop sequences comprise three cysteine residues separated by two loop sequences, the first of which comprises 4 amino acids and the second of which comprises 6 amino acids and the amino acid sequence comprises:

$C_i{}^L/_N$YSPC$_{ii}$WHPLN$^D/_K$C$_{iii}$ (SEQ ID NO: 5), wherein $C_i$, $C_{ii}$ and $C_{ii}$ represent first, second and third cysteine residues, respectively, or a modified derivative, or a pharmaceutically acceptable salt thereof.

In a further embodiment, the peptide ligand of $C_i{}^L/_N$YSPC$_{ii}$WHPLN$^D/_K$C$_{iii}$ (SEQ ID NO: 5) comprises an amino acid sequence selected from:

$C_i$LYSPC$_{ii}$WHPLNDC$_{iii}$; (SEQ ID NO: 6)
and $C_i$NYSPC$_{ii}$WNHPLNKC$_{iii}$; (SEQ ID NO: 7)

wherein $C_i$, $C_{ii}$ and $C_{iii}$ represent first, second and third cysteine residues, respectively, or a modified derivative, or a pharmaceutically acceptable salt thereof.

In a yet further embodiment, said loop sequences comprise three cysteine residues separated by two loop sequences, the first of which comprises 4 amino acids and the second of which comprises 6 amino acids and the amino acid sequence has N- and/or C-terminal modifications and comprises:
[Biot]-G-[Sar5]-A-(SEQ ID NO: 6)-A (herein referred to as BCY10482);
A-(SEQ ID NO: 6)-A-[Sar6]-[KBiot] (herein referred to as BCY10549);
A-(SEQ ID NO: 6)-A-K(Pya) (herein referred to as BCY11607);
Ac-A-(SEQ ID NO: 6)-A-K(Pya) (hereinafter referred to as BCY12708);
A-(SEQ ID NO: 6)-A (herein referred to as BCY10351);
A-(SEQ ID NO: 7)-A-[Sar6]-[KBiot] (herein referred to as BCY11501); and
A-(SEQ ID NO: 7)-A (herein referred to as BCY10729), such as:
[Biot]-G-[Sar5]-A-(SEQ ID NO: 6)-A (herein referred to as BCY10482);
A-(SEQ ID NO: 6)-A-[Sar6]-[KBiot] (herein referred to as BCY10549);
A-(SEQ ID NO: 6)-A-K(Pya) (herein referred to as BCY11607); and
A-(SEQ ID NO: 7)-A-[Sar6]-[KBiot] (herein referred to as BCY11501),
wherein Pya represents 4-pentynoyl moiety.

In a yet further embodiment, said loop sequences comprise three cysteine residues separated by two loop sequences, the first of which comprises 4 amino acids and the second of which comprises 6 amino acids and the amino acid sequence has N- and/or C-terminal modifications and comprises:
A-(SEQ ID NO: 6)-A-K(Pya) (herein referred to as BCY11607); and
Ac-A-(SEQ ID NO: 6)-A-K(Pya) (hereinafter referred to as BCY12708);
wherein Pya represents 4-pentynoyl moiety.

In one embodiment, said loop sequences comprise three cysteine residues separated by two loop sequences, the first of which comprises 4 amino acids and the second of which comprises 8 amino acids and the amino acid sequence comprises:

$C_iEWISC_{ii}PGEPHRWWC_{iii}$; (SEQ ID NO: 41)

$CiVWEAC_{ii}PEHPDQWWC_{iii}$; (SEQ ID NO: 42)

$C_iSTWHC_{ii}FWNLQEGKC_{iii}$; (SEQ ID NO: 43)

$C_iEWKAC_{ii}EHDRERWWC_{iii}$; (SEQ ID NO: 44)

$C_iKTWDC_{ii}FWASQVSEC_{iii}$; (SEQ ID NO: 46)

$C_iSTWQC_{ii}FYDLQEGHC_{iii}$; (SEQ ID NO: 47)

$CiTTWEChFYDLQEGHC_{iii}$; (SEQ ID NO: 48)

$C_iETWEC_{ii}FWRLQAGEC_{iii}$; (SEQ ID NO: 49)

$C_iRTWQC_{ii}FWDLQEGLC_{iii}$; (SEQ ID NO: 50)

$C_iSTWQC_{ii}FWDSQLGAC_{iii}$; (SEQ ID NO: 51)

$C_iETWEC_{ii}FWEWQVGSC_{iii}$; (SEQ ID NO: 52)

$C_iTTWEC_{ii}FWDLQEGLC_{iii}$; (SEQ ID NO: 53)

$C_iHTWDC_{ii}FYQWQDGHC_{iii}$; and (SEQ ID NO: 54)

$C_iTTWEC_{ii}FYSLQDGHC_{iii}$; (SEQ ID NO: 55)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than one or more or all of SEQ ID NOS: 41-55.

In a further embodiment, said loop sequences comprise three cysteine residues separated by two loop sequences, the first of which comprises 4 amino acids and the second of which comprises 8 amino acids and the amino acid sequence has N- and/or C-terminal modifications and comprises:
  A-(SEQ ID NO: 41)-A (herein referred to as BCY10339);
  A-(SEQ ID NO: 42)-A (herein referred to as BCY10340);
  A-(SEQ ID NO: 43)-A (herein referred to as BCY10342);
    A-(SEQ ID NO: 44)-A (herein referred to as BCY10345);
  A-(SEQ ID NO: 45)-A (herein referred to as BCY10347);
  A-(SEQ ID NO: 46)-A (herein referred to as BCY10348);
  A-(SEQ ID NO: 47)-A (herein referred to as BCY10720);
  A-(SEQ ID NO: 48)-A (herein referred to as BCY10721);
  A-(SEQ ID NO: 49)-A (herein referred to as BCY10722);
  A-(SEQ ID NO: 50)-A (herein referred to as BCY10723);
  A-(SEQ ID NO: 51)-A (herein referred to as BCY10724);
  A-(SEQ ID NO: 52)-A (herein referred to as BCY10725);
  A-(SEQ ID NO: 53)-A (herein referred to as BCY10726);
  A-(SEQ ID NO: 54)-A (herein referred to as BCY10727); and
  A-(SEQ ID NO: 55)-A (herein referred to as BCY10728).

In one embodiment, said loop sequences comprise three cysteine residues separated by two loop sequences, both of which comprise 5 amino acids and the amino acid sequence comprises:

$C_iNEDMYC_{ii}FMWMEC_{iii}$; (SEQ ID NO: 56)

$C_iLYEYDC_{ii}YTWRRC_{iii}$; (SEQ ID NO: 57)

$C_iRYEYDC_{ii}HTWQRC_{iii}$; (SEQ ID NO: 58)

$C_iWYEYDC_{ii}TTWERC_{iii}$; (SEQ ID NO: 59)

$C_iWYEYDC_{ii}RTWTRC_{iii}$; (SEQ ID NO: 60)

$C_iLYEYDC_{ii}HTWTRC_{iii}$; and (SEQ ID NO: 61)

$C_iWYEYDC_{ii}RTWTFC_{iii}$; (SEQ ID NO: 62)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than one or more or all of SEQ ID NOS: 56-62.

In a further embodiment, said loop sequences comprise three cysteine residues separated by two loop sequences, both of which comprise 5 amino acids and the amino acid sequence has N- and/or C-terminal modifications and comprises:
  A-(SEQ ID NO: 56)-A (herein referred to as BCY10360);
  A-(SEQ ID NO: 57)-A (herein referred to as BCY10363);
  A-(SEQ ID NO: 58)-A (herein referred to as BCY10732);
  A-(SEQ ID NO: 59)-A (herein referred to as BCY10733);
  A-(SEQ ID NO: 60)-A (herein referred to as BCY10734);
  A-(SEQ ID NO: 61)-A (herein referred to as BCY10735); and
  A-(SEQ ID NO: 62)-A (herein referred to as BCY10736).

In an alternative embodiment, said loop sequences comprise three cysteine residues separated by two loop sequences, both of which comprise 5 amino acids and the amino acid sequence comprises:

$C_iWYEYDC_{ii}NNWERC_{iii}$, (SEQ ID NO: 8)

wherein $C_i$, $C_{ii}$ and $C_{iii}$ represent first, second and third cysteine residues, respectively, or a modified derivative, or a pharmaceutically acceptable salt thereof.

In a further embodiment, said loop sequences comprise three cysteine residues separated by two loop sequences, both of which comprise 5 amino acids and the amino acid sequence has N- and/or C-terminal modifications and comprises:
  A-(SEQ ID NO: 8)-A-[Sar6]-[KBiot] (herein referred to as BCY10550); and
  A-(SEQ ID NO: 8)-A (herein referred to as BCY10361), such as:
    A-(SEQ ID NO: 8)-A-[Sar6]-[KBiot] (herein referred to as BCY10550).

In one embodiment, said loop sequences comprise three cysteine residues separated by two loop sequences, the first of which comprises 5 amino acids and the second of which comprises 7 amino acids and the amino acid sequence comprises:

$C_i$HGGVWC$_{ii}$IPNINDSC$_{iii}$; (SEQ ID NO: 63)

$C_i$DSPVRC$_{ii}$YVVNTQKGC$_{iii}$; (SEQ ID NO: 64)
and $C_i$GSPVPC$_{ii}$YVVNTRKGC$_{iii}$; (SEQ ID NO: 65)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than one or more or all of SEQ ID NOS: 63-65.

In a further embodiment, said loop sequences comprise three cysteine residues separated by two loop sequences, the first of which comprises 5 amino acids and the second of which comprises 7 amino acids and the amino acid sequence has N- and/or C-terminal modifications and comprises:
  A-(SEQ ID NO: 63)-A (herein referred to as BCY10336);
  A-(SEQ ID NO: 64)-A (herein referred to as BCY10337); and
  A-(SEQ ID NO: 65)-A (herein referred to as BCY10338).

In one embodiment, said loop sequences comprise three cysteine residues separated by two loop sequences, the first of which comprises 6 amino acids and the second of which comprises 5 amino acids and the amino acid sequence comprises:

$C_i$APFEFNC$_{ii}$YTWRPC$_{iii}$; (SEQ ID NO: 66)

$C_i$RVLYSPC$_{ii}$YHWLNC$_{iii}$; (SEQ ID NO: 67)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than either or both of SEQ ID NOS: 66-67.

In a further embodiment, said loop sequences comprise three cysteine residues separated by two loop sequences, the first of which comprises 6 amino acids and the second of which comprises 5 amino acids and the amino acid sequence has N- and/or C-terminal modifications and comprises:
  A-(SEQ ID NO: 66)-A (herein referred to as BCY10346); and
  A-(SEQ ID NO: 67)-A (herein referred to as BCY10357).

In an alternative embodiment, said loop sequences comprise three cysteine residues separated by two loop sequences, the first of which comprises 6 amino acids and the second of which comprises 5 amino acids and the amino acid sequence comprises:
  $C_i$VIRYSPC$_{ii}$SHYLNC$_{iii}$ (SEQ ID NO: 9),
wherein $C_i$, $C_{ii}$ and $C_{iii}$ represent first, second and third cysteine residues, respectively, or a modified derivative, or a pharmaceutically acceptable salt thereof.

In a further embodiment, said loop sequences comprise three cysteine residues separated by two loop sequences, the first of which comprises 6 amino acids and the second of which comprises 5 amino acids and the amino acid sequence has N- and/or C-terminal modifications and comprises:
  A-(SEQ ID NO: 9)-A-[Sar6]-[KBiot] (herein referred to as BCY10794); and
  A-(SEQ ID NO: 9)-A (herein referred to as BCY10349), such as:
  A-(SEQ ID NO: 9)-A-[Sar6]-[KBiot] (herein referred to as BCY10794).

In one embodiment, said loop sequences comprise three cysteine residues separated by two loop sequences, both of which comprise 6 amino acids and the amino acid sequence comprises:

$C_i$SIMYSPC$_{ii}$EHPHNHC$_{iii}$; (SEQ ID NO: 68)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than SEQ ID NO: 68.

In a further embodiment, said loop sequences comprise three cysteine residues separated by two loop sequences, both of which comprise 6 amino acids and the amino acid sequence has N- and/or C-terminal modifications and comprises:
  A-(SEQ ID NO: 68)-A (herein referred to as BCY10362).

In one embodiment, said loop sequences comprise three cysteine residues separated by two loop sequences, the first of which comprises 8 amino acids and the second of which comprises 3 amino acids and the amino acid sequence comprises:

$C_i$DKWEPDHLC$_{ii}$YWWC$_{iii}$; (SEQ ID NO: 69)

$C_i$DAWPETHVC$_{ii}$YWWC$_{iii}$; (SEQ ID NO: 70)
and $C_i$DEYTPEHLC$_{ii}$YWWC$_{iii}$; (SEQ ID NO: 71)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than one or more or all of SEQ ID NOS: 69-71.

In a further embodiment, said loop sequences comprise three cysteine residues separated by two loop sequences, the first of which comprises 8 amino acids and the second of which comprises 3 amino acids and the amino acid sequence has N- and/or C-terminal modifications and comprises:
  A-(SEQ ID NO: 69)-A (herein referred to as BCY10332);
  A-(SEQ ID NO: 70)-A (herein referred to as BCY10717); and
  A-(SEQ ID NO: 71)-A (herein referred to as BCY10718).

In an alternative embodiment, said loop sequences comprise three cysteine residues separated by two loop sequences, the first of which comprises 8 amino acids and the second of which comprises 3 amino acids and the amino acid sequence comprises:

$C_i$DYSPWWHPC$_{ii}$NHIC$_{iii}$, (SEQ ID NO: 10)

wherein $C_i$, $C_{ii}$ and $C_{iii}$ represent first, second and third cysteine residues, respectively, or a modified derivative, or a pharmaceutically acceptable salt thereof.

In a further embodiment, said loop sequences comprise three cysteine residues separated by two loop sequences, the first of which comprises 8 amino acids and the second of which comprises 3 amino acids and the amino acid sequence has N- and/or C-terminal modifications and comprises:

[Biot]-G-[Sar5]-A-(SEQ ID NO: 10)-A (herein referred to as BCY11369); and
A-(SEQ ID NO: 10)-A (herein referred to as BCY10331), such as:
[Biot]-G-[Sar5]-A-(SEQ ID NO: 10)-A (herein referred to as BCY11369).

In one embodiment, said loop sequences comprise three cysteine residues separated by two loop sequences, the first of which comprises 8 amino acids and the second of which comprises 4 amino acids and the amino acid sequence comprises:

$C_i$WINYSISPC$_{ii}$GEC$_{iii}$; (SEQ ID NO: 72)
and
$C_i$RYEYPEHLC$_{ii}$YTWQC$_{iii}$; (SEQ ID NO: 73)

wherein $C_i$, $C_{ii}$ and $C_{iii}$ represent first, second and third cysteine residues, respectively, or a modified derivative, or a pharmaceutically acceptable salt thereof.

In one embodiment, the peptide of the invention is other than either or both of SEQ ID NOS: 72-73.

In a further embodiment, said loop sequences comprise three cysteine residues separated by two loop sequences, the first of which comprises 8 amino acids and the second of which comprises 4 amino acids and the amino acid sequence has N- and/or C-terminal modifications and comprises:

A-(SEQ ID NO: 72)-A (herein referred to as BCY10334); and
A-(SEQ ID NO: 73)-A (herein referred to as BCY10719).

In a yet further embodiment, the amino acid sequence is selected from BCY10551, BCY10552, BCY10479, BCY11371, BCY10482, BCY10549, BCY11501, BCY10550, BCY10794 and BCY11369. The peptides of this embodiment were tested in the OX40 cell-based assay and demonstrated good agonism of OX40 (see Table 2).

In a yet further embodiment, the amino acid sequence is selected from BCY10551, BCY11371 and BCY10549. Such peptides demonstrated EC$_{50}$ values of less than 100 nM in the OX40 cell-based assay, demonstrating particularly high levels of agonism (see Table 2).

In a yet further embodiment, the amino acid sequence is BCY10549. This peptide when bound to streptavidin in a tetrameric format demonstrated an EC$_{50}$ values of less than 20 nM in the OX40 cell-based assay and demonstrated high levels of OX40 agonism (see FIG. 1 and Table 2).

In an alternative embodiment, the amino acid sequence is BCY11607.

In an alternative embodiment, the amino acid sequence is BCY12708.

In a further embodiment, the pharmaceutically acceptable salt is selected from the free acid or the sodium, potassium, calcium or ammonium salt.

Unless defined otherwise, all technical and scientific terms used herein have the same meaning as commonly understood by those of ordinary skill in the art, such as in the arts of peptide chemistry, cell culture and phage display, nucleic acid chemistry and biochemistry.

Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$h ed., John Wiley & Sons, Inc.), which are incorporated herein by reference.

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

$$-C_i-I_i-L_2-W_3-C_{ii}-N_4-P_5-E_6-P_7-H_8-D_9-E_{10}-C_{iii}-.$$ (SEQ ID NO: 1)

For the purpose of this description, all bicyclic peptides are assumed to be cyclised with 1,1',1"-(1,3,5-triazinane-1,3,5-triyl)triprop-2-en-1-one (TATA) and yielding a tri-substituted structure. Cyclisation with TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal biotin-G-Sar$_5$ tail would be denoted as:

[Biot]-G-[Sar5]-A-(SEQ ID NO: X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus become C-terminus and vice versa) and their stereochemistry is likewise also reversed (i.e. D-amino acids become L-amino acids and vice versa).

Peptide Ligand Definition

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons. (for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulphur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the DLL3 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labelled reagent in place of the non-labelled reagent previously employed.

Molecular Scaffold

In one embodiment, the molecular scaffold comprises a non-aromatic molecular scaffold. References here in "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an αβ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606).

Multimeric Binding Complexes

According to one aspect of the invention, there is provided a multimeric binding complex which comprises at least two peptide ligands, wherein at least one peptide ligand is specific for OX40 as defined herein and said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

The present invention describes a series of multimerized bicyclic peptides with various chemical linkers and hinges of various lengths and rigidity using different sites of attachments within said bicyclic peptide which bind and activate targets (such as OX40) with a wide range of potency and efficacy.

It will be appreciated by the skilled person that the concept of the invention is the recognition that multiply arranged (multimeric) bicyclic peptides provide a synergistic benefit by virtue of the resultant properties of said multimeric binding complexes compared to the corresponding monomeric binding complexes which contain a single bicyclic peptide. For example, the multimeric binding complexes of the invention typically have greater levels of binding potency or functional activity (as measured herein by $EC_{50}$ values) than their monomeric counterparts. Furthermore, the multimeric binding complexes of the invention are designed to be sufficiently small enough to be cleared by the kidneys.

The complexes of the present invention find particular utility in the treatment of cancer. Thus, in one embodiment, at least one of said peptide ligands is specific for an epitope present on a T cell or a cancer cell. In a further embodiment, each of said peptide ligands is specific for an epitope present on a T cell or a cancer cell.

In a particular embodiment, at least one of said peptide ligands is specific for OX40 and at least one of said further peptide ligands binds to a further component on an immune cell. In a further embodiment, said further component on an immune cell is CD137. Thus, in a yet further embodiment, at least one of said peptide ligands comprises a CD137 binding peptide ligand.

In further embodiments, at least one of said peptide ligands is specific for OX40 and at least one of said further peptide ligands binds to a component present on a cancer cell. Thus, in certain embodiments, multimerized peptides of the invention comprise at least one peptide ligand specific for OX40, at least one peptide ligand which binds to a component present on a cancer cell and optionally at least one peptide ligand which binds to a component on an immune cell. In further embodiments, multimerized peptides of the invention comprise at least one peptide ligand specific for OX40, at least one peptide ligand which binds to a further component on an immune cell and optionally at least one peptide ligand which binds to a component present on a cancer cell.

In further embodiments, the immune cell is selected from: white blood cells; lymphocytes (e.g. T lymphocytes or T cells, B cells or natural killer cells); CD8 or CD4; CD4; dendritic cells, follicular dendritic cells and granulocytes. In particular embodiments, at least one of said peptide ligands is specific for OX40 and the immune cell is a CD4 T cell. In further embodiments, the immune cell is selected from a CD4 T cell and a CD8 cell. In yet further embodiments, the immune cell is selected from a CD4 T cell and another immune cell.

Without being bound by theory it is believed that multimerized peptides are able to activate receptors by homo-crosslinking more than one of the same receptor. Thus, in one embodiment, said peptide ligands are specific for the same target. In a further embodiment, the multimeric binding complex comprises at least two identical peptide ligands. By "identical" it is meant peptides having the same amino acid sequence, most critically the same amino acid sequence refers to the binding portion of said peptide (for example, the sequence may vary in attachment position). In this embodiment, each of the peptides within the multimeric binding complex will bind exactly the same epitope upon the same target—the resultant target bound complex will therefore create a homodimer (if the multimeric complex comprises two identical peptides), homotrimer (if the multimeric complex comprises three identical peptides) or homotetramer (if the multimeric complex comprises four identical peptides), etc.

In an alternative embodiment, the multimeric binding complex comprises at least two differing peptide ligands. By "differing" it is meant peptides having a different amino acid sequence. In this embodiment, the differing peptide ligands within the multimeric binding complex will bind to different epitopes on the same target—the resultant target bound complex will therefore create a biparatopic (if the multimeric complex comprises two differing peptides), triparatopic (if the multimeric complex comprises three differing peptides) or tetraparatopic (if the multimeric complex comprises four differing peptides), etc.

Without being bound by theory it is believed that multimerized peptides are able to activate receptors by heterocrosslinking differing targets, such as differing target receptors. Thus, in one embodiment, said peptide ligands are specific for different targets. It will be appreciated that in this embodiment, the multimeric binding complex comprises at least two differing peptide ligands (i.e. peptide ligands having differing amino acid sequences). In this embodiment, each of the peptides within the multimeric binding complex will bind a differing epitope upon a different target—the resultant target bound complex will therefore create a bispecific multimeric binding complex (if the multimeric complex comprises two differing peptides), trispecific multimeric binding complex (if the multimeric complex comprises three differing peptides), tetraspecific multimeric binding complex (if the multimeric complex comprises four differing peptides), etc.

It will be appreciated that the multimeric binding complexes of the invention may be designed to be capable of binding to a range of different targets, such as receptors. Suitable examples include any target (i.e. receptor) involved in a cancer, such as members of the TNF receptor superfamily (i.e. CD137), receptor tyrosine kinase (RTK), Ig domain receptors (immune checkpoint) etc. It will be appreciated that for the bi-, tri- and tetra-specific multimeric binding complexes referred to hereinbefore the peptides may bind to targets on at least two differing cells (such as T, NK or other immune cells).

The peptides within the multimeric binding complexes of the invention may be assembled via a number of differing options. For example, there may be a central hinge or branching moiety with spacer or arm elements radiating from said hinge or branch point each of which will contain a peptide. Alternatively, it could be envisaged that a circular support member may hold a number of inwardly or outwardly projecting peptides.

In one embodiment, each peptide ligand is connected to a central hinge moiety by a spacer group.

It will be appreciated that the spacer group may be linear and connect a single peptide with the central hinge moiety. Thus, in one embodiment, the multimeric binding complex comprises a compound of formula (I):

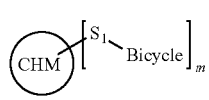
(I)

wherein CHM represents a central hinge moiety;
$S_1$ represents a spacer group;
Bicycle represents a peptide ligand as defined herein; and
m represents an integer selected from 2 to 10.

In one embodiment, m represents an integer selected from 3 to 10. In a further embodiment, m represents an integer selected from 3 or 4.

When m represents 4, it will be appreciated that the central hinge moiety will require 4 points of attachment. Thus, in one embodiment, m represents 4 and CHM is a motif of formula (A):

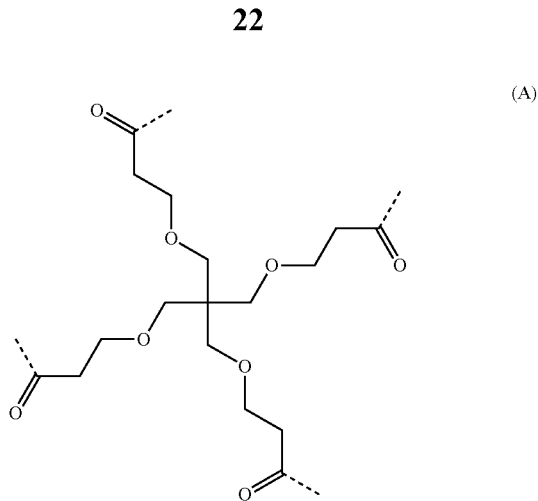
(A)

wherein "-----" represents the point of attachment to each $S_1$ group.

When m represents 3, it will be appreciated that the central hinge moiety will require 3 points of attachment. Thus, in one embodiment, m represents 3 and CHM is a motif of formula (B):

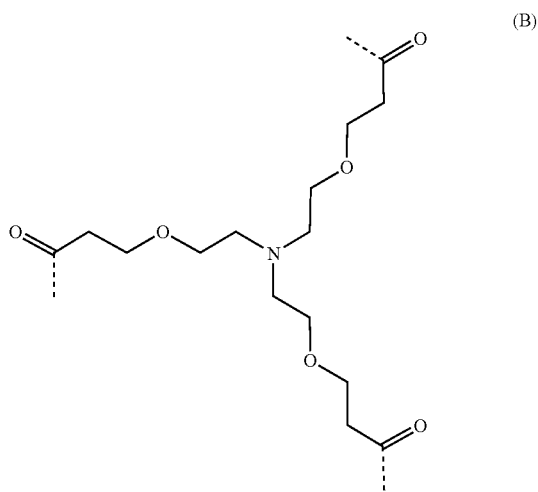
(B)

wherein "-----" represents the point of attachment to each $S_1$ group.

In an alternative embodiment, m represents 3 and CHM is a motif of formula (C):

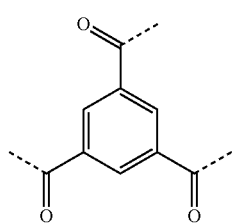
(C)

wherein "-----" represents the point of attachment to each $S_1$ group.

In an alternative embodiment, m represents 3 and CHM is a motif of formula (D):

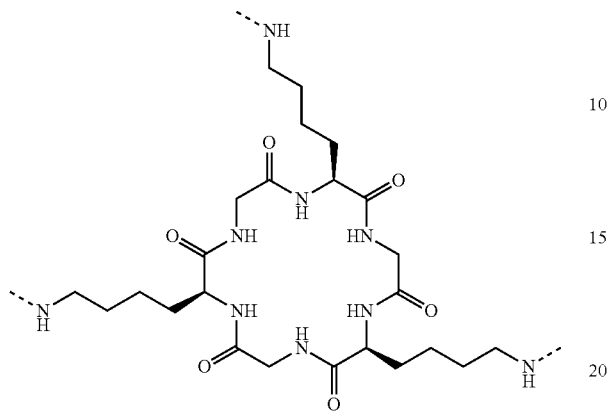

(D)

wherein "-----" represents the point of attachment to each $S_1$ group.

It will be readily apparent to the skilled person how alternative central hinge moieties may be constructed depending upon the value of m.

It will be appreciated that the spacer ($S_1$) may be any suitable construction to link the peptide central hinge moiety to the peptide. In one embodiment, the spacer ($S_1$) comprises a triazolyl moiety. The advantage of this embodiment is that the triazolyl moiety may be incorporated within the synthesis using commonly available "click" chemistry. Examples of suitable spacer ($S_1$) groups include one or more PEG moieties, peptide sequences, carbohydrates, lipids and the like.

In a further embodiment, the spacer ($S_1$) comprises one or more PEG moieties. References herein to "PEG" refer to a linear polymer with a regular repeat unit of the general structure: $(CH_2CH_2O)_n$— (where n represents any number, such as 1 to 30).

Thus, in a further embodiment, the spacer ($S_1$) is selected from any one of spacers $S_1A$, $S_1B$, $S_1C$, $S_1D$, $S_1E$, $S_1F$, $S_1G$ and $S_1H$:

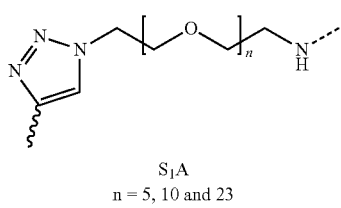

$S_1A$
n = 5, 10 and 23

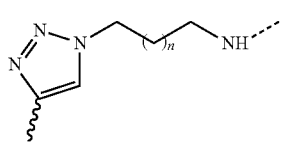

$S_1E$
n = 1

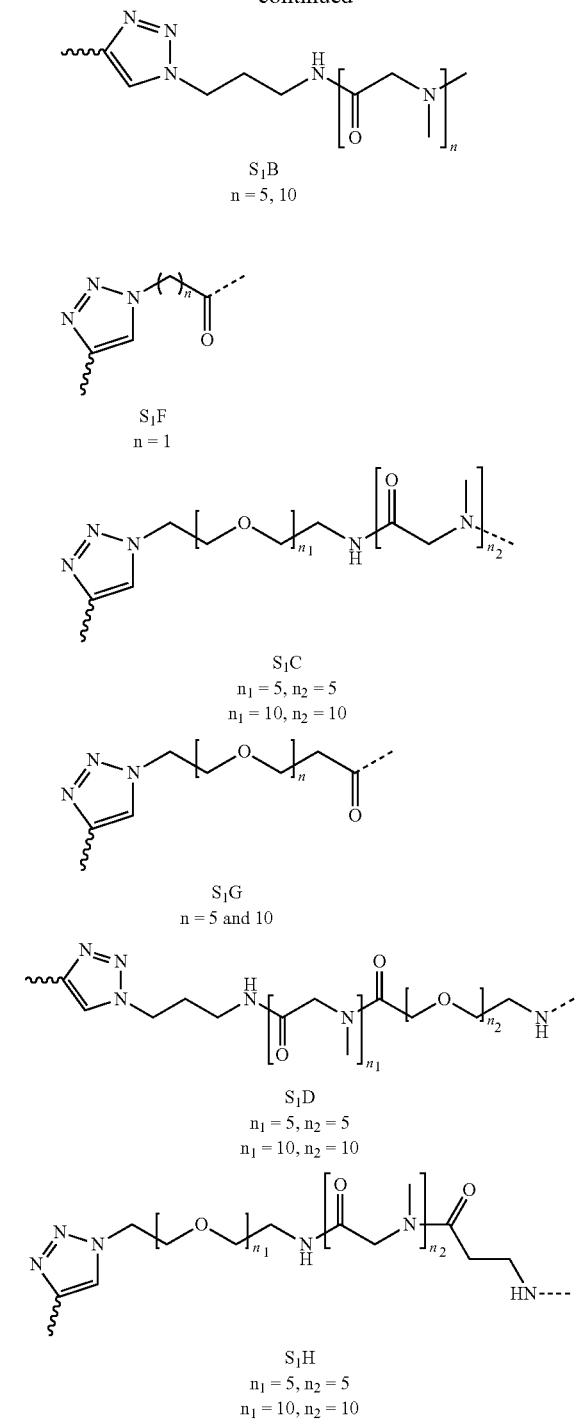

-continued $S_1B$
n = 5, 10

$S_1F$
n = 1

$S_1C$
$n_1 = 5, n_2 = 5$
$n_1 = 10, n_2 = 10$ $S_1G$
n = 5 and 10

$S_1D$
$n_1 = 5, n_2 = 5$
$n_1 = 10, n_2 = 10$ $S_1H$
$n_1 = 5, n_2 = 5$
$n_1 = 10, n_2 = 10$ wherein "-----" represents the point of attachment to the CHM group; and

 represents the point of attachment to the Bicycle group.

In a yet further embodiment, the spacer ($S_1$) is $S_1A$.

Tetramers

In one embodiment, the multimeric binding complex comprises a tetrameric binding complex described in the following Table 1:

TABLE 1

Exemplified Tetrameric Binding Complexes of the Invention

| Multimer Compound Number | Corresponding Monomer | Number of Monomers | Central Hinge Moiety | Spacer Molecule | Attachment Point |
|---|---|---|---|---|---|
| BCY12019 | BCY11607 | 4 | A (TET) | $S_1A$: n = 23 | C-terminal Lys(PYA) |

Data is presented herein which demonstrates that the tetrameric binding complex of Table 1 displayed $EC_{50}$ improvement relative to the monomeric OX40 ligand (see Table 2).

In a further embodiment, the multimeric binding complex comprises a tetramer comprising four bicyclic peptides each of which are BCY11607 as defined herein, which is linked via the C-terminal Lys(PYA) moiety to a spacer molecule $(S_1A)$ wherein n represents 23 and wherein $(S_1A)$ is linked to a central hinge moiety which is (A) as defined herein. This multimeric binding complex is referred to herein as BCY12019:

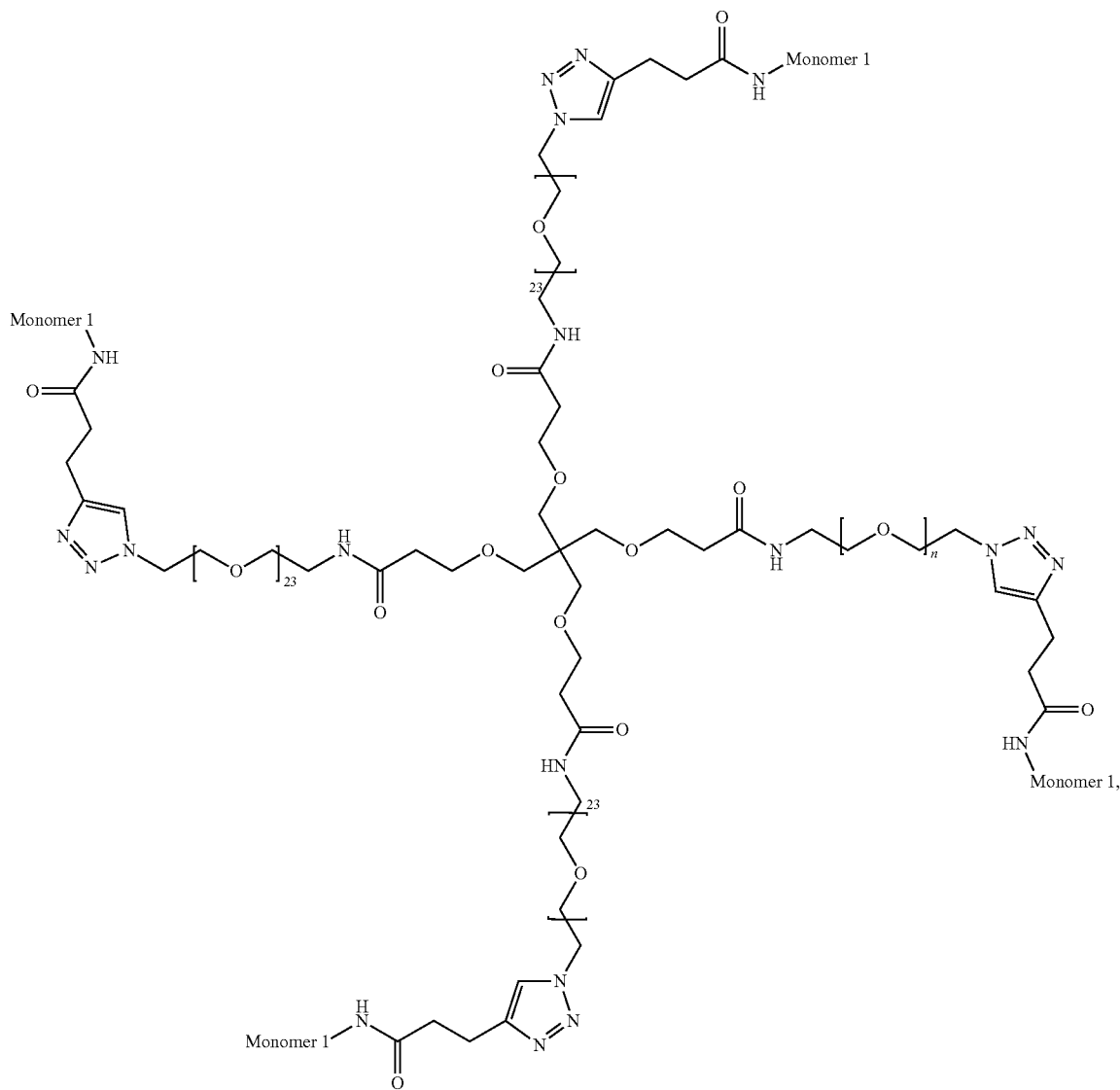

BCY12019 wherein Monomer 1 represents BCY11607.

Data is presented herein in Table 2 which shows almost 10 fold greater agonism compared with the corresponding biotinylated monomer (BCY10549).

In an alternative arrangement the spacer group may be branched and thus a single spacer group may connect multiple peptides with the central hinge moiety. Thus, in an alternative embodiment, the multimeric binding complex comprises a compound of formula (II):

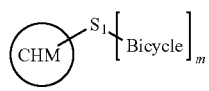

(II)

wherein CHM represents a central hinge moiety;
$S_1$ represents a spacer group;
Bicycle represents a peptide ligand as defined herein; and
m represents an integer selected from 2 to 10.

It will be appreciated that the peptide ligand may be attached to the spacer via a number of means. In one embodiment, the peptide ligand is conjugated to one half of a binding pair and said other half of said binding pair links each of the peptides to the spacer.

In one embodiment, said binding pair comprises biotin and streptavidin. Thus, each peptide ligand is conjugated to biotin and linked to the spacer via streptavidin.

Heterotandems

In one embodiment, the multimeric binding complex is a heterotandem bicyclic peptide complex comprising:
(a) one or more OX40 binding peptide ligands as defined herein; conjugated via a linker to
(b) at least one second peptide ligand which binds to a component present on a cancer cell;
wherein each of said peptide ligands comprises a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

In a further embodiment, the multimeric binding complex is a heterotandem bicyclic peptide complex comprising:
(a) an OX40 binding peptide ligand as defined herein; conjugated via a linker to
(b) a second peptide ligand which binds to a component present on a cancer cell; wherein each of said peptide ligands comprises a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

References herein to the term "cancer cell" includes any cell which is known to be involved in cancer. Cancer cells are created when the genes responsible for regulating cell division are damaged. Carcinogenesis is caused by mutation and epimutation of the genetic material of normal cells, which upsets the normal balance between proliferation and cell death. This results in uncontrolled cell division and the evolution of those cells by natural selection in the body. The uncontrolled and often rapid proliferation of cells can lead to benign or malignant tumours (cancer). Benign tumours do not spread to other parts of the body or invade other tissues. Malignant tumours can invade other organs, spread to distant locations (metastasis) and become life-threatening.

In one embodiment, the cancer cell is selected from an HT1080, SC-OV-3, PC3, H1376, NCI-H292, LnCap, MC38, 4T1-D02 and RKO tumour cell.

In one embodiment, the component present on a cancer cell is EphA2. In a further embodiment, the second peptide ligand comprises an EphA2 binding bicyclic peptide ligand.

In an alternative embodiment, the component present on a cancer cell is PD-L1. In a further embodiment, the second peptide ligand comprises a PD-L1 binding bicyclic peptide ligand.

In an alternative embodiment, the component present on a cancer cell is Nectin-4. In a further embodiment, the second peptide ligand comprises a Nectin-4 binding bicyclic peptide ligand. In a yet further embodiment, the Nectin-4 binding bicyclic peptide ligand comprises an amino acid having the sequence:

CP[1Nal][dD]CM[HArg]DWSTP[HyP]WC (SEQ ID NO: 11; hereinafter referred to as BCY8116), wherein 1Nal represents 1-naphthylalanine, HArg represents homoarginine and HyP represents hydroxyproline.

In a still yet further embodiment, the Nectin-4 binding bicyclic peptide ligand is selected from a PEG12 derivative of BCY8116, a PEG5 derivative of BCY8116 and a trifunctional PEG3 derivative of BCY8116.

In one embodiment, the heterotandem comprises one OX40 binding peptide and one second peptide ligand which binds to a component present on a cancer cell. In an alternative embodiment, the heterotandem comprises two OX40 binding peptides and one second peptide ligand which binds to a component present on a cancer cell. It will be appreciated that when the heterotandem comprises more than one OX40 binding peptide that each OX40 binding peptide may either be the same sequence or a differing sequence. In one embodiment, when the heterotandem comprises more than one OX40 binding peptide, each OX40 binding peptide comprises the same sequence.

In a still yet further embodiment, the OX40 binding peptide ligand is BCY11607 and the Nectin-4 binding bicyclic peptide ligand is a PEG12 derivative of BCY8116 which has the following structure:

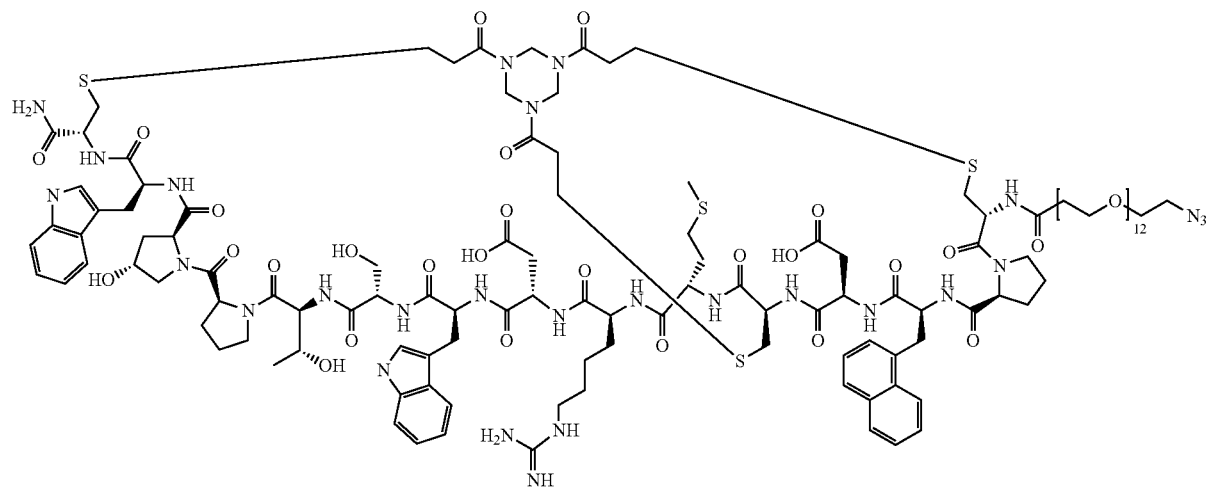
and the resultant heterotandem complex has the following structure:
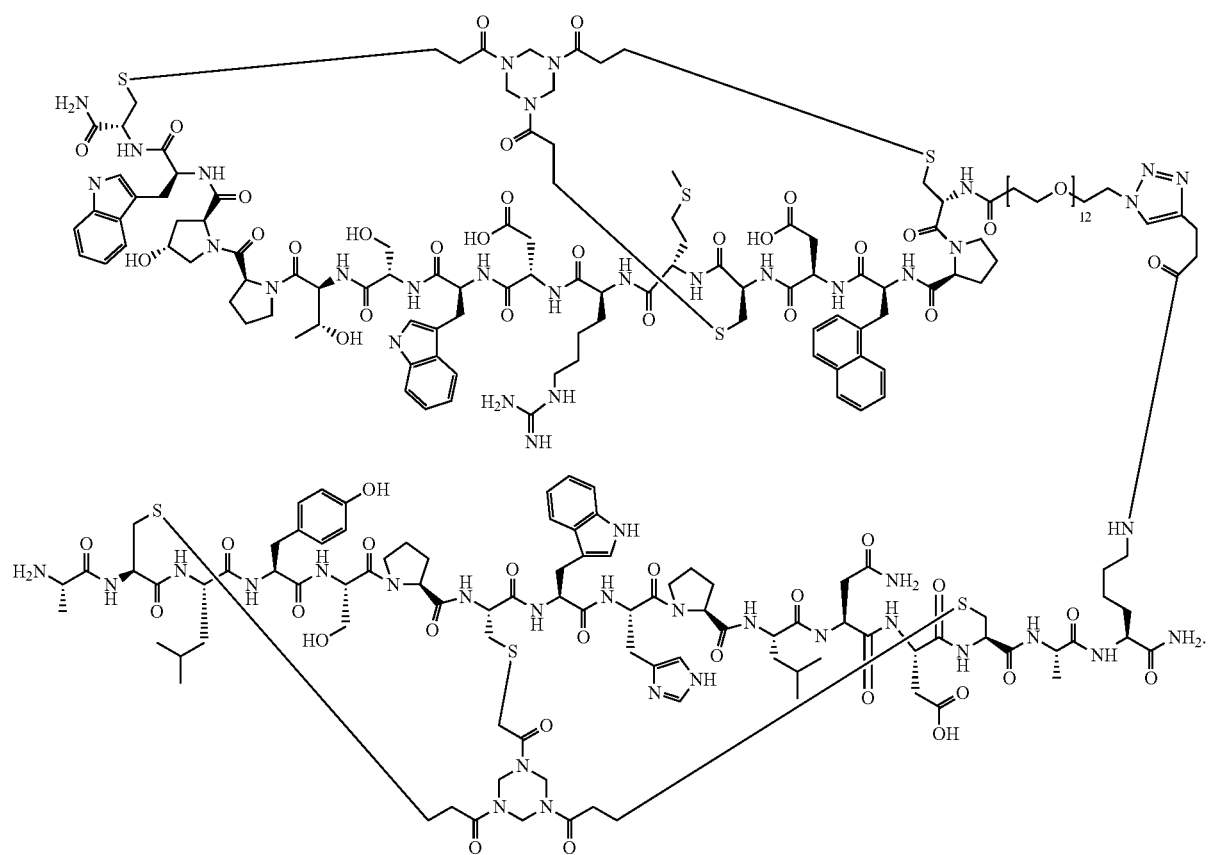

In an alternative embodiment, the OX40 binding peptide ligand is BCY12708 and the Nectin-4 binding bicyclic peptide ligand is a PEG5 derivative of BCY8116 which has the following structure:
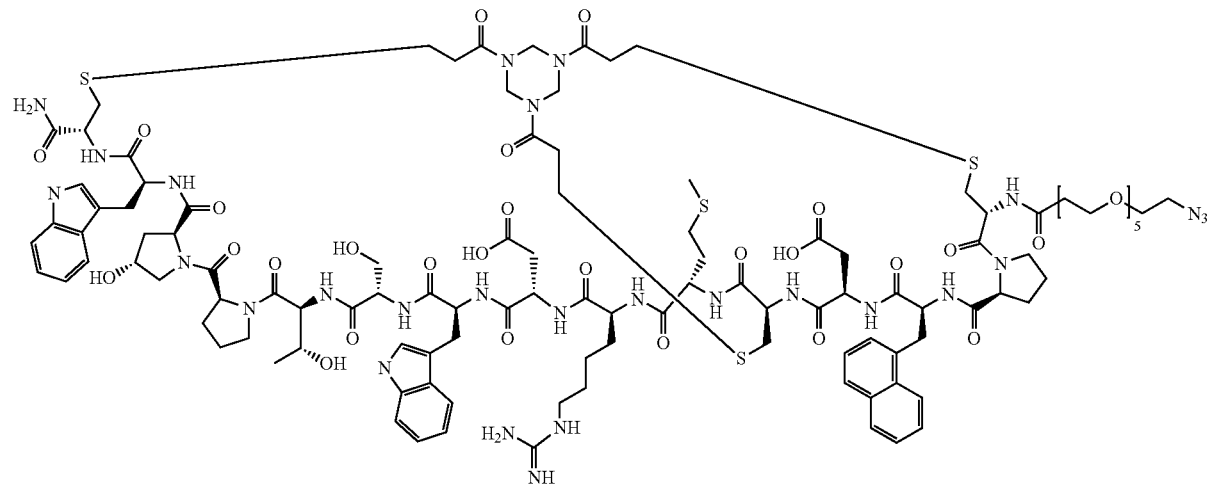
and the resultant heterotandem complex has the following structure:
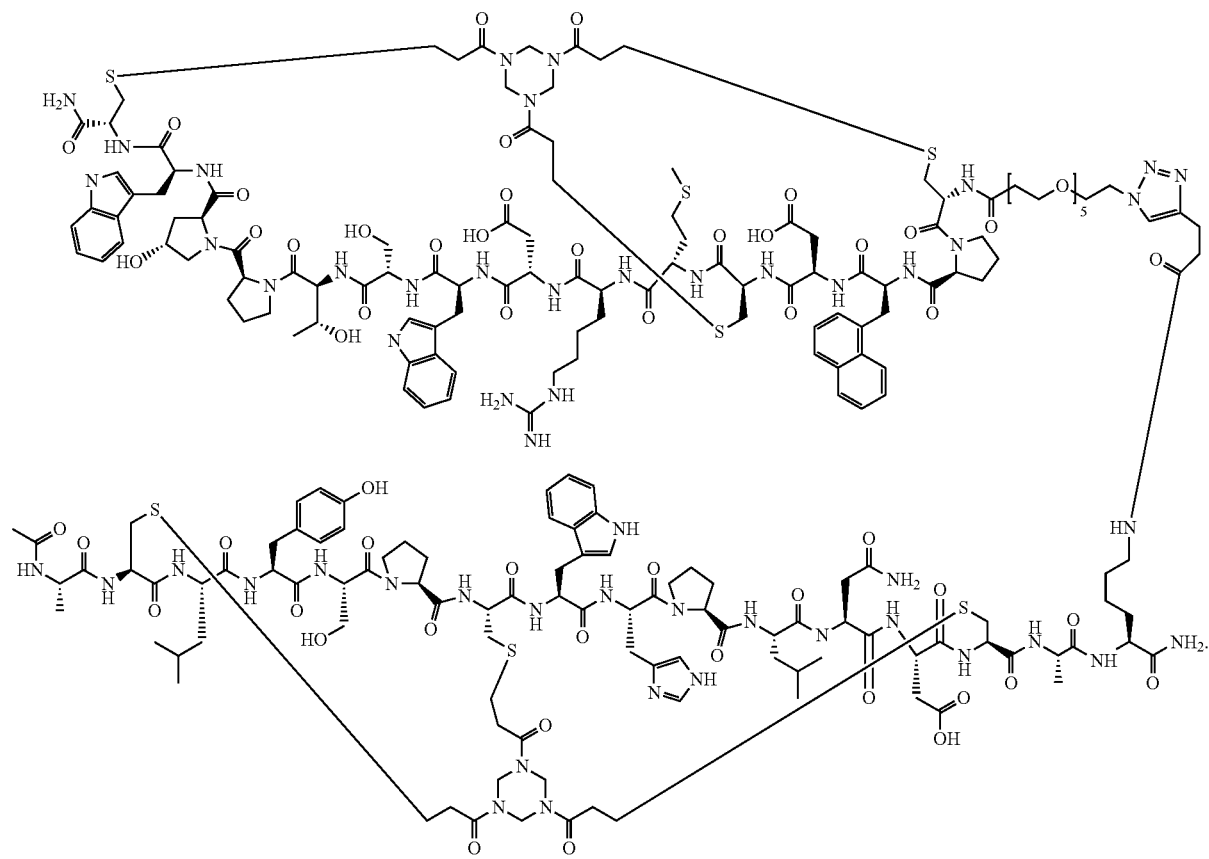
BCY12721

In a still yet further embodiment, the OX40 binding peptide ligand is BCY11607 and the Nectin-4 binding bicyclic peptide ligand is a trifunctional PEG3 derivative of BCY8116 which has the following structure:
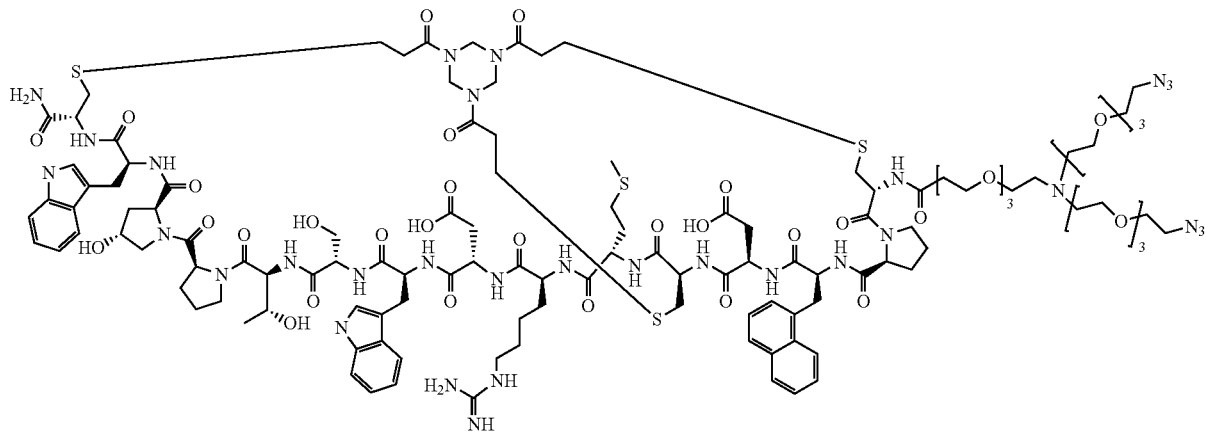
and the resultant heterotandem complex has the following structure:
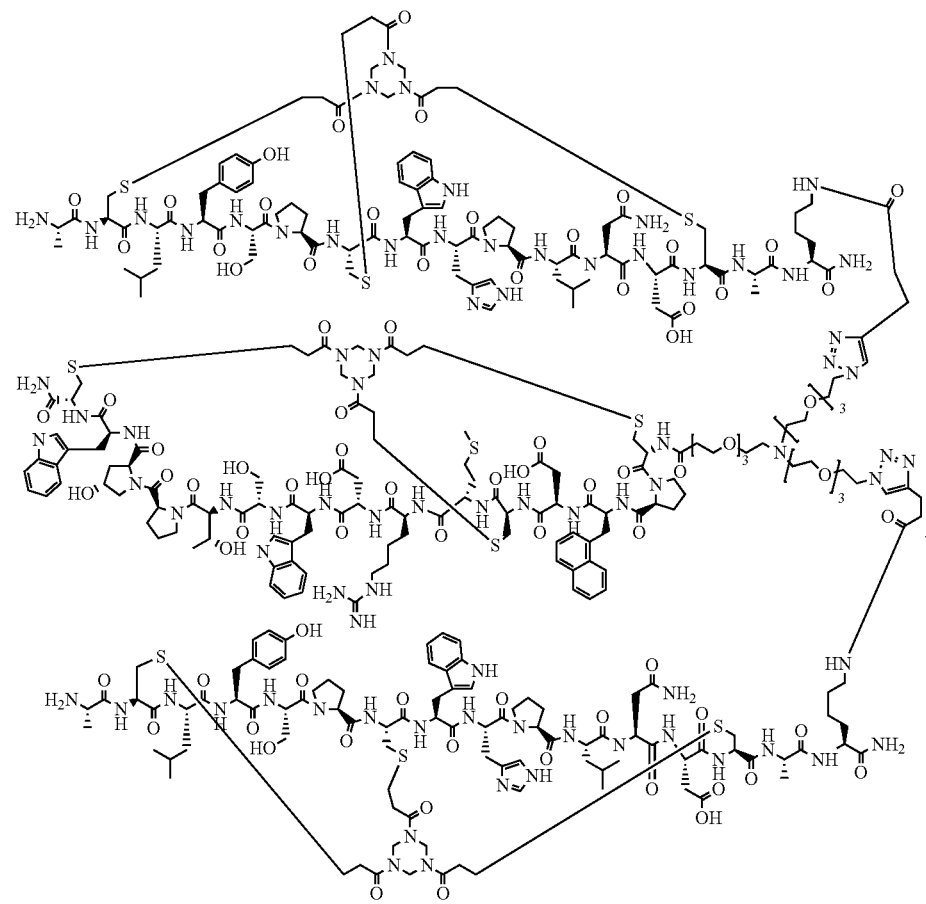
BCY12697

In one embodiment, the heterotandem bicyclic peptide complex is selected from BCY12141, BCY12721 and BCY12967. Data is presented herein in Table 3 and FIG. 3 wherein these Nectin-4:OX40 compounds showed potent OX40 agonism when in co-culture with Nectin-4 positive 4T1-D02 cells as compared to OX40L and non-binding control peptide BCY12968.

In an alternative embodiment, the component present on a cancer cell is prostate-specific membrane antigen (PSMA). In a further embodiment, the second peptide ligand comprises a PSMA binding bicyclic peptide ligand.

Linkers

It will be appreciated that the OX40 peptide ligand may be conjugated to the second peptide ligand via any suitable linker. Typically the design of said linker will be such that the two Bicyclic peptides are presented in such a manner that they can bind unencumbered to their respective targets either alone or while simultaneously binding to both target receptors. Additionally, the linker should permit binding to both targets simultaneously while maintaining an appropriate distance between the target cells that would lead to the desired functional outcome. The properties of the linker may be modulated to increase length, rigidity or solubility to optimise the desired functional outcome. The linker may also be designed to permit the attachment of more than one Bicycle to the same target. Increasing the valency of either binding peptide may serve to increase the affinity of the heterotandem for the target cells or may help to induce oligomerisation of one or both of the target receptors.

In one embodiment, the linker is selected from the following sequences: —CH$_2$—, -PEG$_5$-, -PEG$_{10}$-, -PEG$_{12}$-, -PEG$_{23}$-, -PEG$_{24}$-, -PEG$_{15}$-Sar$_5$-, -PEG$_{10}$-Sar$_{10}$-, -PEG$_5$-Sar$_{15}$-, -PEG$_5$-Sar$_5$-, -B-Ala-Sar$_{20}$-, -B-Ala-Sar$_{10}$-PEG$_{10}$-, -B-Ala-Sar$_5$-PEG$_{15}$- and -B-Ala-Sar$_5$-PEG$_5$-.

Structural representations of suitable linkers are detailed below:

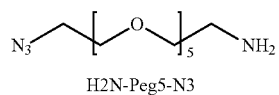

H2N-Peg5-N3

COM00000132

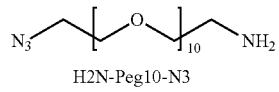

H2N-Peg10-N3

COM00000134

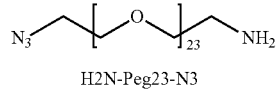

H2N-Peg23-N3

COM00000135

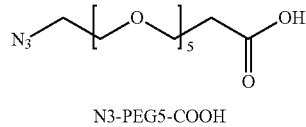

N3-PEG5-COOH

COM00000467

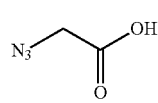

N3-CH2-COOH

COM00000468

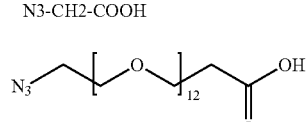

N3-PEG12-COOH

COM00000466

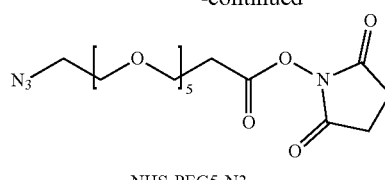

NHS-PEG5-N3

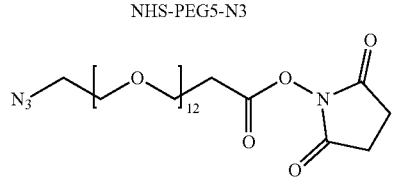

NHS-PEG12-N3

COM00000128

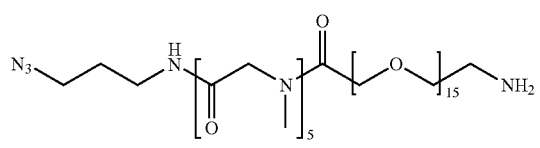

H2N-PEG15-SAR5-N3

COM00000129

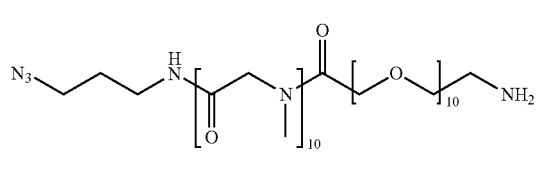

H2N-PEG10-SAR10-N3

COM00000130

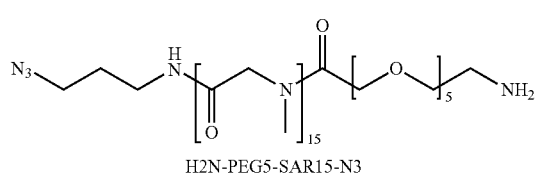

H2N-PEG5-SAR15-N3

COM00000131

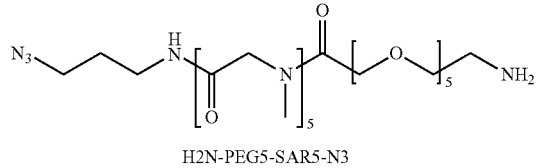

H2N-PEG5-SAR5-N3

COM00000469

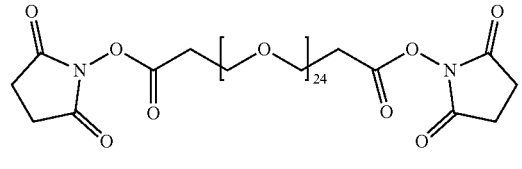

NHS-PEG24-NHS

COM00000470

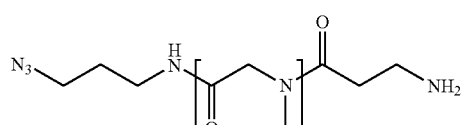

H2N-(B-Ala)-SAR20-N3

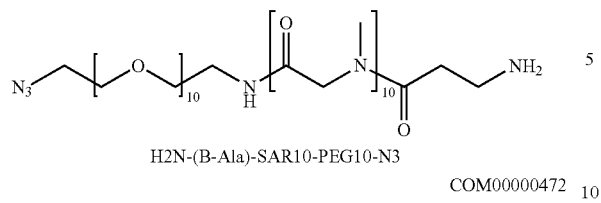
H2N-(B-Ala)-SAR10-PEG10-N3
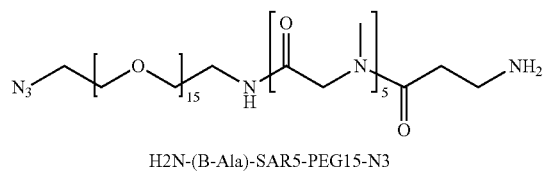
H2N-(B-Ala)-SAR5-PEG15-N3
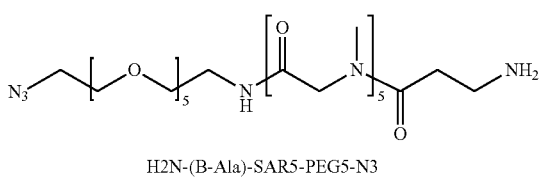
H2N-(B-Ala)-SAR5-PEG5-N3
In one embodiment, the linker is a branched linker to allow one first peptide at one end and the two or more second peptides at the other end.
In a further embodiment, the branched linker is selected from:
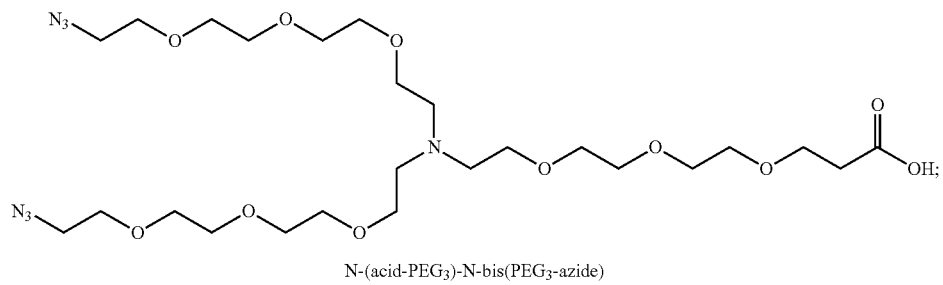
N-(acid-PEG$_3$)-N-bis(PEG$_3$-azide)
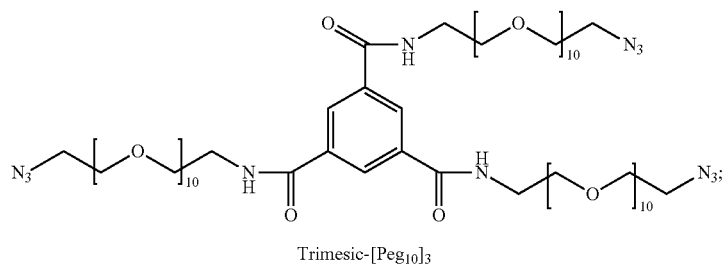
Trimesic-[Peg$_{10}$]$_3$
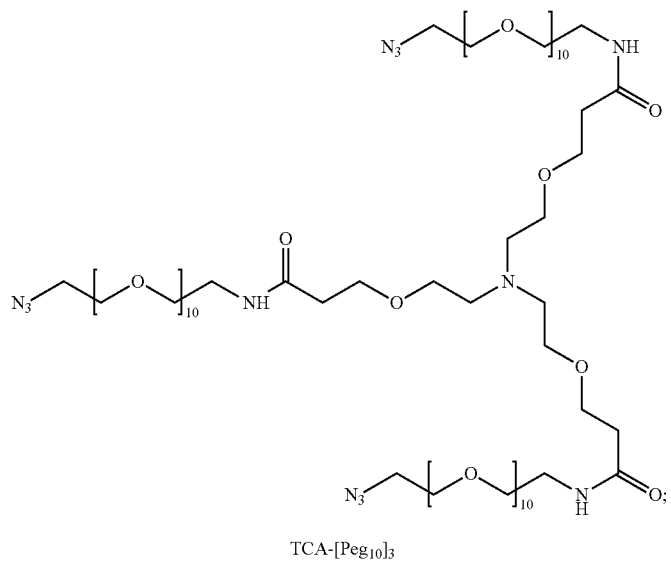
TCA-[Peg$_{10}$]$_3$

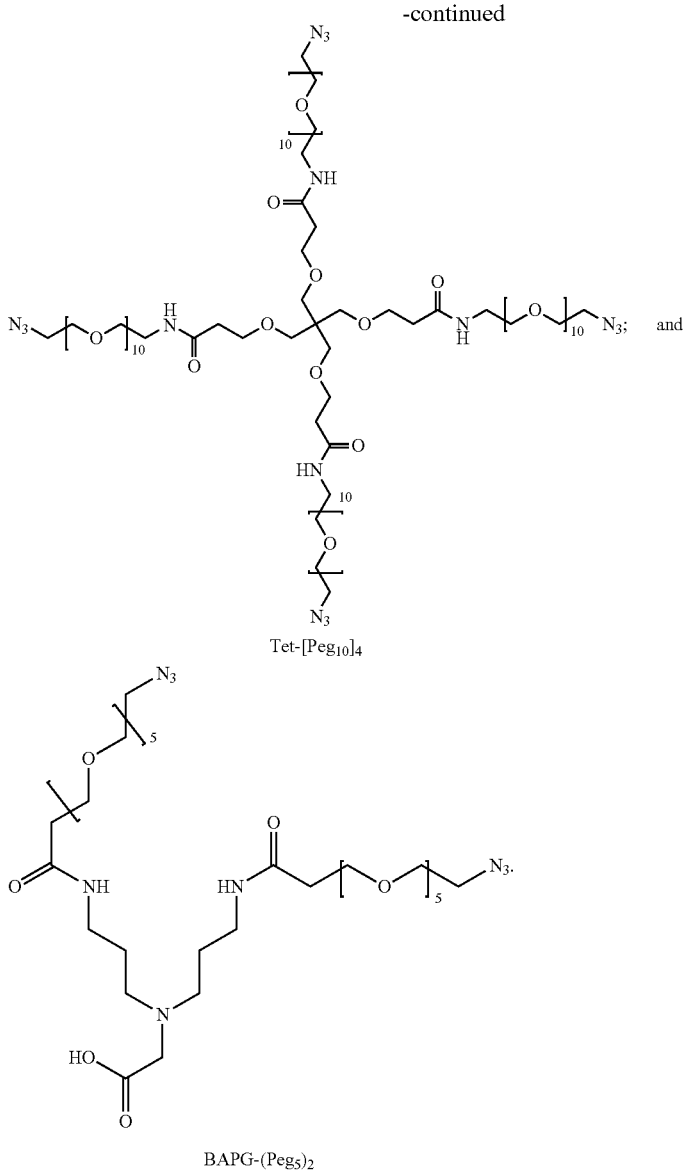

Tet-[Peg10]4

BAPG-(Peg5)2

In a further embodiment, the linker is selected from $N_3$—$PEG_5$-COOH, $N_3$—$PEG_{12}$-COOH and N-(acid-$PEG_3$)-N-bis($PEG_3$-azide).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to the manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Drug Conjugates

According to a further aspect of the invention, there is provided a drug conjugate comprising a peptide ligand or multimeric binding complex as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetrating peptide from *Drosophila* Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one embodiment, the multimeric binding complexes of the invention contain a cleavable bond, such as a disulphide bond or a protease sensitive bond. Without being bound by theory it is believed that such a cleavable moiety deactivates the complex until it reaches the tumour microenvironment. The benefit of this embodiment provides for the complex to be reduced in size following binding to the target. In a further embodiment, the groups adjacent to the disulphide bond are modified to control the hindrance of the disulphide bond, and by this the rate of cleavage and concomitant release of the binding agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on the targeting entity (here, the bicyclic peptide).

Pharmaceutical Compositions

According to a further aspect of the invention, there is provided a pharmaceutical composition comprising a peptide ligand, multimeric binding complex or drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as OX40 binding agents. According to a further aspect of the invention, there is provided a peptide ligand, multimeric binding complex, drug conjugate or pharmaceutical composition as defined herein for use in preventing, suppressing or treating a disease or disorder mediated by OX40.

The OX40 receptor (also known as Tumour necrosis factor receptor superfamily, member 4 (TNFRSF4) and also known as CD134 receptor), is a member of the TNFR-superfamily of receptors which is not constitutively expressed on resting naïve T cells, unlike CD28. OX40 is a secondary co-stimulatory immune checkpoint molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels.

OX40 has no effect on the proliferative abilities of CD4+ cells for the first three days, however after this time proliferation begins to slow and cells die at a greater rate; due to an inability to maintain a high level of PKB activity and expression of Bcl-2, Bcl-XL and survivin. OX40L binds to OX40 receptors on T-cells, preventing them from dying and subsequently increasing cytokine production. OX40 has a critical role in the maintenance of an immune response beyond the first few days and onwards to a memory response due to its ability to enhance survival. OX40 also plays a crucial role in both Th1 and Th2 mediated reactions in vivo.

OX40 binds TRAF2, 3 and 5 as well as PI3K by an unknown mechanism. TRAF2 is required for survival via NF-κB and memory cell generation whereas TRAF5 seems to have a more negative or modulatory role, as knockouts have higher levels of cytokines and are more susceptible to Th2-mediated inflammation. TRAF3 may play a critical role in OX40-mediated signal transduction. CTLA-4 is down-regulated following OX40 engagement in vivo and the OX40-specific TRAF3 DN defect was partially overcome by CTLA-4 blockade in vivo. TRAF3 may be linked to OX40-mediated memory T cell expansion and survival, and point to the down-regulation of CTLA-4 as a possible control element to enhance early T cell expansion through OX40 signaling.

In one embodiment, the OX40 is mammalian OX40. In a further embodiment, the mammalian OX40 is human OX40 (hOX40).

OX40 peptides will be primarily (but not exclusively) used to agonistically activate OX40, and consequently immune cells, to prevent, suppress or treat cancer such as early or late stage human malignancies, which includes solid tumours such as Non-Small Cell Lung Carcinomas (NSCLC), breast cancers, including triple negative breast cancers (TNBC), ovarian cancers, prostate cancers, bladder cancers, urothelial carcinomas, colorectal cancers, head and neck cancer, Squamous Cell Carcinoma of the Head and Neck (SCCHN), melanomas, pancreatic cancers, and other advanced solid tumours where immune suppression blocks anti-tumour immunity. Other solid and non-solid malignancies where OX40 peptides will be used as a therapeutic agent includes, but not limited to, B-cell lymphoma including low grade/follicular non-Hodgkin's lymphoma and Acute Myeloid Leukemia (AML).

References herein to solid tumour in this embodiment is defined as an abnormal growth of tissues without much liquid mass in it, while non-solid tumours are generally dispersed cancers without any or significant solid masses. Examples of solid tumours are carcinomas, sarcomas and lymphomas. Blood cancers (Leukemias) such as acute myeloid leukemia (AML), Acute lymphocytic (or lymphoblastic) leukemia (ALL) are non-solid tumours, OX40 peptides will be used as a monotherapy agent in the aforementioned cancer indications to boost CD4, CD8 T cell and NK cell-mediated anti-tumour immunity and immune cell-mediated killing of tumour cells. In addition, to use as a monotherapy agent in cancer, OX40 peptides, and its conjugates such a tumour targeting heterotandems will be used in combination with other immunotherapy agents, including but not limited to, such as anti-PD- and anti-CTLA4. Additional therapeutic applications of OX40 peptides include, but are not restricted to, mono or combination immunotherapies with radiation cancer treatments, and cancer vaccines. Non-cancerous therapeutic applications of OX40 peptides either as monotherapy or in combination with other immunomodulatory drugs such as anti-PD-1, includes but are not limited to, viral infections such as HIV and HPV.

It will be appreciated that the multimeric binding complex defined herein which comprises at least one peptide ligand which binds to a component present on a cancer cell will be useful in the treatment of cancer.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Monomeric Peptide Synthesis

Monomeric peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-Triacryloyl-hexahydro-1,3,5-triazine (TATA, Sigma). For this, linear peptide was diluted with 50:50 MeCN:$H_2O$ up to ~35 mL, ~500 µL of 100 mM TATA in acetonitrile was added, and the reaction was initiated with 5 mL of 1 M $NH_4HCO_3$ in $H_2O$. The reaction was allowed to proceed for ~30-60 min at RT, and lyophilised once the reaction had completed (judged by MALDI-MS). Once completed, 1 ml of 1M L-cysteine hydrochloride monohydrate (Sigma) in $H_2O$ was added to the reaction for ~60 min at RT to quench any excess TATA.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

Multimeric Binding Complex Synthesis

The multimeric binding complexes described herein may be prepared in an analogous manner to that described in International Patent Application Number PCT/GB2019/050485 (WO 2019/162682).

Preparation of BCY12019

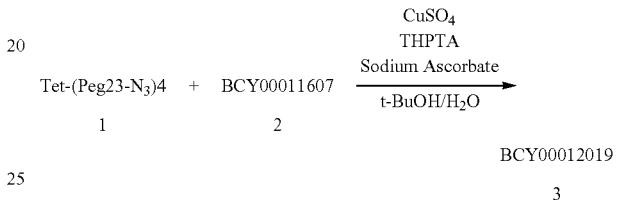

A mixture of compound 1 (described in PCT/GB2019/050485 (WO 2019/162682); 10 mg, 2.11 µmol, 1.0 eq.), BCY11607 (18.5 mg, 8.63 µmol, 4.1 eq.), and THPTA (3.7 mg, 8.42 µmol, 4.0 eq.) was dissolved in t-BuOH/$H_2O$ (1:1, 2 mL, pre-degassed and purged with $N_2$ for 3 times). $CuSO_4$ (21.0 µL, 0.4 M, 4.0 eq.) and Sodium ascorbate (42.0 µL, 0.4 M, 8.0 eq.) were added under $N_2$. The pH of this solution was adjusted to 8 by dropwise addition of 0.2 M $NH_4HCO_3$ (in 1:1 t-BuOH/$H_2O$). The reaction mixture was stirred at 40° C. for 4 hr, when LC-MS showed compound 1 was completely consumed and one main peak with desired m/z (calculated MW: 13347.41, observed m/z: 1213.83 ([M/11+H]$^+$) was detected. The reaction mixture was concentrated under reduced pressure to remove solvent and purified by prep-HPLC (TFA condition) to obtain BCY12019 (8.2 mg, 0.54 µmol, 25.9% yield, 88.8% purity) as a white solid.

Heterotandem Binding Complex Synthesis

The heterotandem binding complexes described herein may be prepared in an analogous manner to that described in International Patent Application Number PCT/GB2019/050951 (WO2019/193328).

Preparation of BCY12141
Procedure for Preparation of BCY8116-PEG12-$N_3$

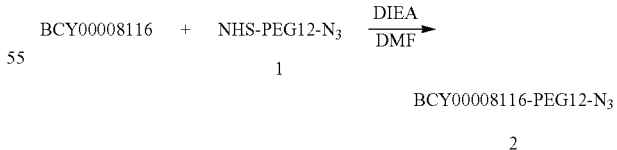

BCY8116 (20.0 mg, 9.21 µmol, 1.0 eq) and compound 1 (11.0 mg, 14.85 µmol, 1.6 eq) were dissolved in DMF (1 mL) and DIEA was added (2.97 mg, 22.96 µmol, 4.0 µl, 2.5 eq), and the mixture was stirred at rt for 2 hr. LC-MS showed BCY8116 was consumed completely and one main peak with desired m/z (calculated MW: 2798.19, observed m/z: 1399.1 ([M/2+H]$^+$)) was detected. The reaction mixture was purified by prep-HPLC (TFA condition) and compound 2 (18.0 mg, 6.09 μmol, 66.13% yield, 94.64% purity) was obtained as a white solid.

Spectra:

Procedure for Preparation of BCY12141

Compound 2 (10.0 mg, 3.57 μmol, 1.0 eq) and BCY11607 (8.0 mg, 3.72 μmol, 1.0 eq) were dissolved in 2 mL of t-BuOH/H$_2$O (1:1), and CuSO$_4$ (0.4 M, 9.0 μL, 1.0 eq), sodium ascorbate (1.0 mg, 5.04 μmol, 1.4 eq) and THPTA (1.4 mg, 3.22 μmol, 1.0 eq) were added and 1 M NH$_4$HCO$_3$ was added to adjust pH to 8. The reaction mixture was stirred at 40° C. for 16 hr under N$_2$ atmosphere. LC-MS showed one main peak with desired m/z (calculated MW: 4947.65, observed m/z: 1237.78 ([M/4+H]$^+$)). The reaction mixture was purified by prep-HPLC (TFA condition) and BCY12141 (8.8 mg, 1.65 μmol, 46.18% yield, 92.78% purity) was obtained as a white solid.

Preparation of BCY12967

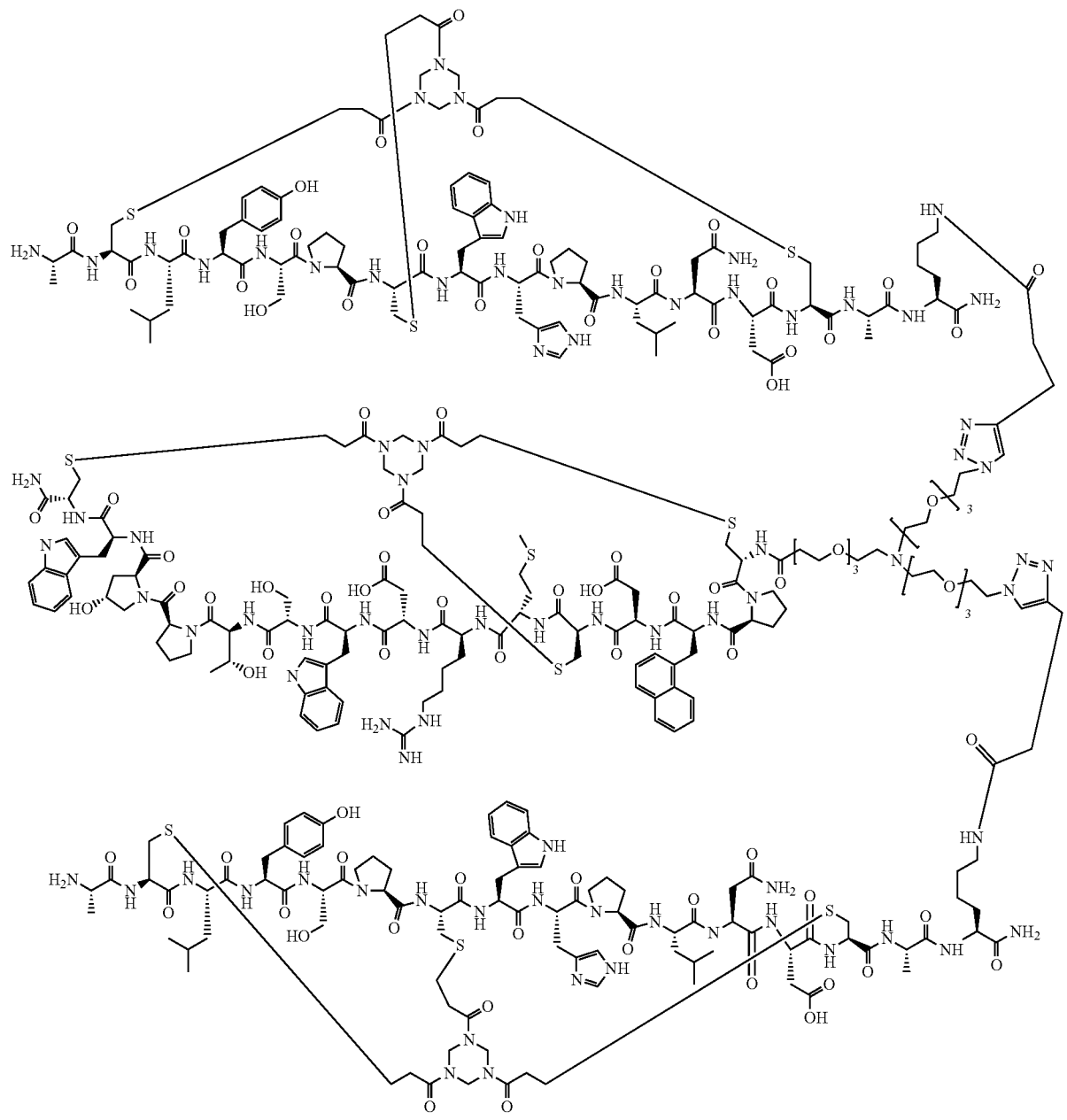

BCY00012967

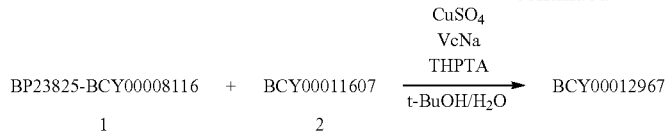

Compound 1 (a trifunctional PEG3 derivative of BCY8116; 20.0 mg, 7.20 μmol, 1.0 eq) and BCY11607 (32.0 mg, 14.9 μmol, 2.1 eq) were first dissolved in 2 mL of t-BuOH/H$_2$O (1:1), and then CuSO$_4$ (0.4 M, 36.0 μL, 2.0 eq), VcNa (6.0 mg, 30.3 μmol, 4.2 eq) and THPTA (6.4 mg, 14.7 μmol, 2.0 eq) were added. Finally 1 M NH$_4$HCO$_3$ was added to adjust pH to 8. All solvents here were degassed and purged with N$_2$ for 3 times. The reaction mixture was stirred at 40° C. for 16 hr under N$_2$ atmosphere. LC-MS showed compound 2 was consumed completely and one main peak with desired m/z (calculated MW: 7077.7 observed m/z: 1416.3 ([M/5+H]$^+$), 1180.4 ([M/6+H]$^+$), 1011.9 ([M/7+H]$^+$)). The reaction mixture was purified by prep-HPLC (TFA condition) and BCY12967 (20.6 mg, 2.82 μmol, 39.17% yield, 96.82% purity) was obtained as a white solid.

Preparation of BCY12721

BCY12721 may be prepared in accordance with analogous procedures to those described herein for BCY12141, BCY12967 and BCY12968.

Biological Data

Promega OX40 Cell-Activity Assay

Promega have developed an OX40 cell-activity assay that uses NF-κB luciferase luminescence as a read-out of OX40 activation in Jurkat cells (Promega CS197704). On the day of the experiment, prepare medium by thawing FBS and adding 5% FBS to RPMI-1640. Thaw OX40 Jurkat cells in the water-bath and then add 500 μl cells to 11.5 ml pre-warmed 5 FBS RPMI-1640 medium. Add 60 μl cells/well to white cell culture plates. Proceed to dilute agonists at concentration giving the maximum fold induction and then titrate down the amount in a sterile 96 well-plate. Suggested starting concentrations are for streptavidin-coupled tetramers is 4×1 μM (1 μM biotin-peptide: 0.25 μM Streptavidin) or 4×100 nM for strong agonists such as synthetic multimers. Prepare enough reagent for duplicate samples and perform ⅓ dilution series or ¹⁄₁₀ dilution series. Include positive control OX40L trimer (R&D systems #1054-OX-010) and negative control monomeric peptide. Add 20 μl of agonist as duplicate samples or 5% FBS RPMI-1640 alone as background control.

Co-incubate cells together with agonists for 5 hours at 37° C., 5% CO$_2$. After 5 hours, thaw Bio-Glo™ and develop the assay at room-temperature. Add 80 μl Bio-Glo™ per well and incubate 5-10 min. Read luciferase signal on CLARIO-Star plate-reader using the MARS program and normalize the fold induction relative to background (medium alone). Analyse data by transforming the data to x=log (X), then plot log (agonist) vs. response variable slope (4 parameters) to calculate EC$_{50}$ values.

The results of this assay are shown in Table 2 where it can be seen that all tested compounds showed good agonism of OX40, in particular BCY10551, BCY11371 and BCY10549 demonstrated particularly high levels of agonism when bound to streptavidin in a tetrameric format. Furthermore, the synthetic multimeric tetravalent compound BCY12019 demonstrated almost 10 fold greater agonism than the corresponding monomer bound to streptavidin in a tetrameric format (BCY10549).

TABLE 2

EC$_{50}$ Values from Promega OX40 cell-activity assay

| Peptide Number | EC$_{50}$ (nM), 2 independent experiments |
|---|---|
| BCY10551 | 59, 19 |
| BCY10552 | 350, 21 |
| BCY10479 | 226, 1300 |
| BCY11371 | 24, 37 |
| BCY10482 | 160, 237 |
| BCY10549 | 17, 19 |
| BCY11501 | 120, 325 |
| BCY10550 | 389, 74 |
| BCY10794 | 186, 102 |
| BCY11369 | 206, 130 |
| BCY12019 | 2.6 |

FIG. 1 also shows data from Promega's OX40 reporter cell assay. BCY10549 in this assay is a biotinylated monomer, which is assembled into a tetravalent agonist by binding to streptavidin. OX40L is used as a positive control for OX40 agonist activity. The synthetic OX40 tetramer BCY12019 showed potent OX40 agonism with EC$_{50}$ in the low nanomolar range in the Promega reporter cell assay. Cross-linking of the biotinylated BCY10549 peptide by streptavidin generated a biologically active complex, whereas the monomeric peptide not bound to streptavidin was inactive.

Promega OX40 Cell-Activity Assay in Co-Culture with Tumor Cells

Promega have developed an OX40 cell-activity assay that uses NF-κB luciferase luminescence as a read-out of OX40 activation in Jurkat cells (Promega CS197704). On the day of the experiment, prepare medium by thawing FBS and adding 5% FBS to RPMI-1640. Thaw OX40 Jurkat cells in the water-bath and then add 500 μl cells to 11.5 ml pre-warmed 5 FBS RPMI-1640 medium. Add 55 μl cells/well to white cell culture plates. Harvest tumor cells from culture. 4T1 is a Nectin-4 negative murine mammary gland epithelial cancer cell and it was genetically modified to express murine Nectin-4 on the cell surface (4T1 Nectin-4 positive; clone 4T1-D02). Tumor cells were cultured to 80% confluency in vitro in RPMI1640 medium supplemented with 10% heat-inactivated FBS, 1× Penicillin/Streptomycin, 1×L-Glutamine, 20 mM HEPES and 1×NEAA (RPMI working medium). Tumor cells were trypsinized and washed two times at 1500 rpm for 5 minutes in RPMI1640 working medium prewarmed to 37° C. Count cells and resuspend at 2,000,000 cells/mL in R5 media (for 10,000 cells/well). Add 5 μL of tumour cells per well.

Proceed to dilute agonists at concentration giving the maximum fold induction and then titrate down the amount in a sterile 96 well-plate. Prepare enough reagent for duplicate samples and then perform ⅓ dilution series or ¹⁄₁₀ dilution series. Include positive control OX40L trimer (AcroBiosystems, R&D systems) and negative control monomeric or non-binding peptides. Add 20 μl of agonist as duplicate samples or 5% FBS RPMI-1640 alone as background control.

Co-incubate cells together with agonists for 6 hours at 37° C., 5% $CO_2$. After 6 hours, thaw Bio-Glo™ and develop the assay at room-temperature. Add 80 μl Bio-Glo™ per well and incubate 5-10 min. Read luciferase signal on CLAIRO-Star plate-reader using the MARS program and normalize the fold induction relative to background (medium alone). Analyse data by transforming the data to x=log (X), then plot log (agonist) vs. response variable slope (4 parameters) to calculate $EC_{50}$ values.

Figure 3:
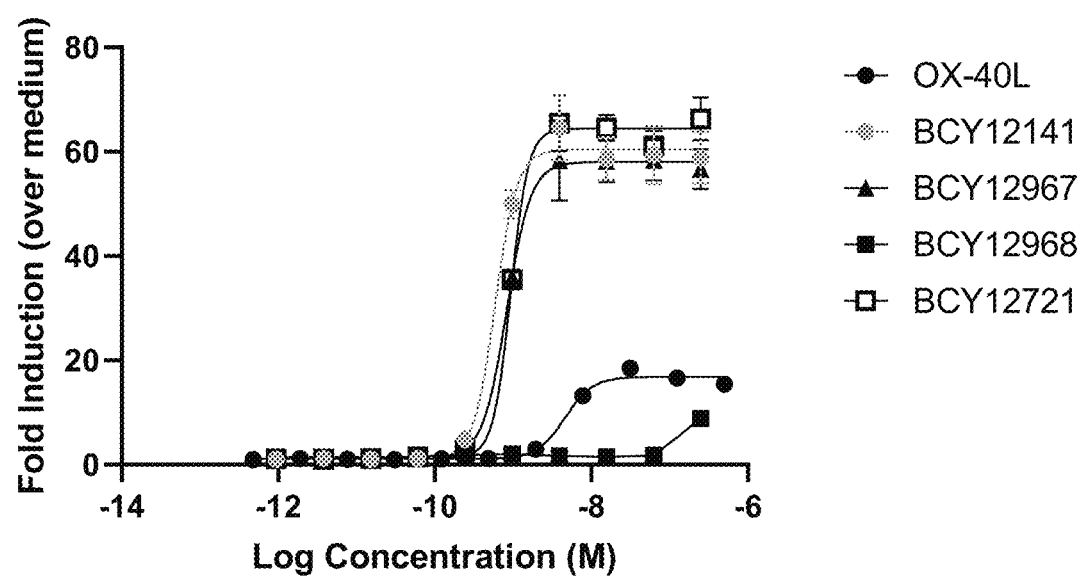
FIG. 3: Results of BCY12141, BCY12721 and BCY12967 in Promega's OX40 cell-activity assay in co-culture with tumor cells in comparison with OX40L and non-binding control peptide BCY12968.

The results of this assay are shown in Table 3 and FIG. 3 where it can be seen that BCY12141, BCY12721 and BCY12967 Nectin-4:OX40 compounds showed potent OX40 agonism when in co-culture with Nectin-4 positive 4T1-D02 cells as compared to OX40L and non-binding control peptide BCY12968.

TABLE 3

$EC_{50}$ Values from Promega OX40 cell-activity assay in co-culture with tumor cells

| Peptide Number | $EC_{50}$ (nM) |
|---|---|
| BCY12141 | 0.59 |
| BCY12967 | 0.83 |
| BCY12721 | 0.94 |

Human PBMC—Tumor Cell Co-Culture Assay for Testing Nectin-4-OX40 Heterotandems In Vitro 4T1, a Nectin-4 negative murine mammary gland epithelial cancer cell (4T1 Nectin-4 −ve; 4T1-Parental) and its genetically modified version expressing murine Nectin-4 on the cell surface (4T1 Nectin-4 +ve; clone 4T1-D02) were cultured to 80% confluency in vitro in RPMI1640 medium supplemented with 10% heat-inactivated FBS, 1× Penicillin/Streptomycin, 1× L-Glutamine, 20 mM HEPES and 1×NEAA (RPMI working medium). Tumor cells were trypsinized and washed two times at 1500 rpm for 5 minutes in RPMI1640 working medium prewarmed to 37° C. Four thousand tumor cells in 25 μl were plated per well in a sterile 384 well cell culture plate. Frozen human PBMCs were thawed and washed one time at 1250 rpm for 5 minutes in prewarmed RPMI1640 working medium. 20000 viable PBMCs in 50 μl RPMI1640 working medium supplemented with 250 ng/ml (2× concentration) of human anti-CD3 (clone OKT3) and 500 ng/ml (2× concentration) of human anti-CD28 (clone CD28.2) were added per respective wells containing tumor cells in 25 μl medium to obtain a 1:10 ratio for tumor cells and PBMCs. Test compounds in DMSO were diluted in RPMI1640 working medium. An equivalent amount of DMSO was added to assay controls. Test compounds were added to cells in 75 μl with 125 ng/ml anti-CD3, 250 ng/ml anti-CD28, 4000 tumor cells, and 20000 PBMCs to a final 100 μl volume. Outer wells in the assay plate were excluded from the study and were filled with RPM1640 working medium. Assay controls include cells treated with anti-CD3 and anti-CD28 alone or Nectine-4 −ve tumor cells co-cultured with test compounds and human PBMCs. Assay plates were incubated inside humidified chambers up to 72 hours. Culture supernatant was collected at 48 hours post-treatment, and IL-2 concentrations were measured using HTRF assays (CIS Bio). Data were analyzed using GraphPad Prism.

Figure 2:
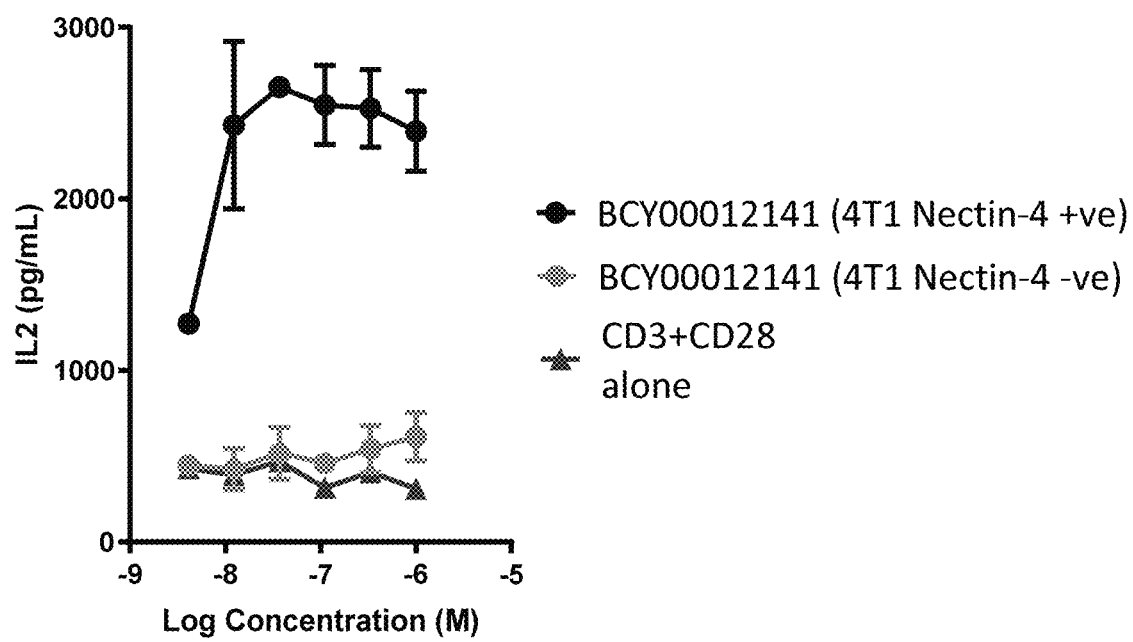
FIG. 2: Results of BCY12141 tested in the PBMC—tumour cell co-culture assay.

The results of the PBMC—tumor cell co-culture assay are shown in FIG. 2. Murine 4T1 tumor cells not expressing or stably expressing murine Nectin4 were co-cultured with human PBMCs and anti-CD3 and anti-CD28 stimulations with or without BCY12141 for 48 hours. Cytokine IL-2 concentrations were then assayed using HTRF. The OX40-Nectin-4 bispecific heterotandem BCY12141 induced the production of the cytokine IL-2 by human PBMCs in the presence of Nectin-4 expressing 4T1 cells. In the absence of Nectin-4 expression on 4T1 cells, the IL-2 levels were comparable to the control baseline CD3+CD28 stimulation. This demonstrates that the OX40-Nectin-4 bispecific molecule BCY12141 is able to induce an immunological response in human PBMCs only in the presence of a cell expressing Nectin-4.

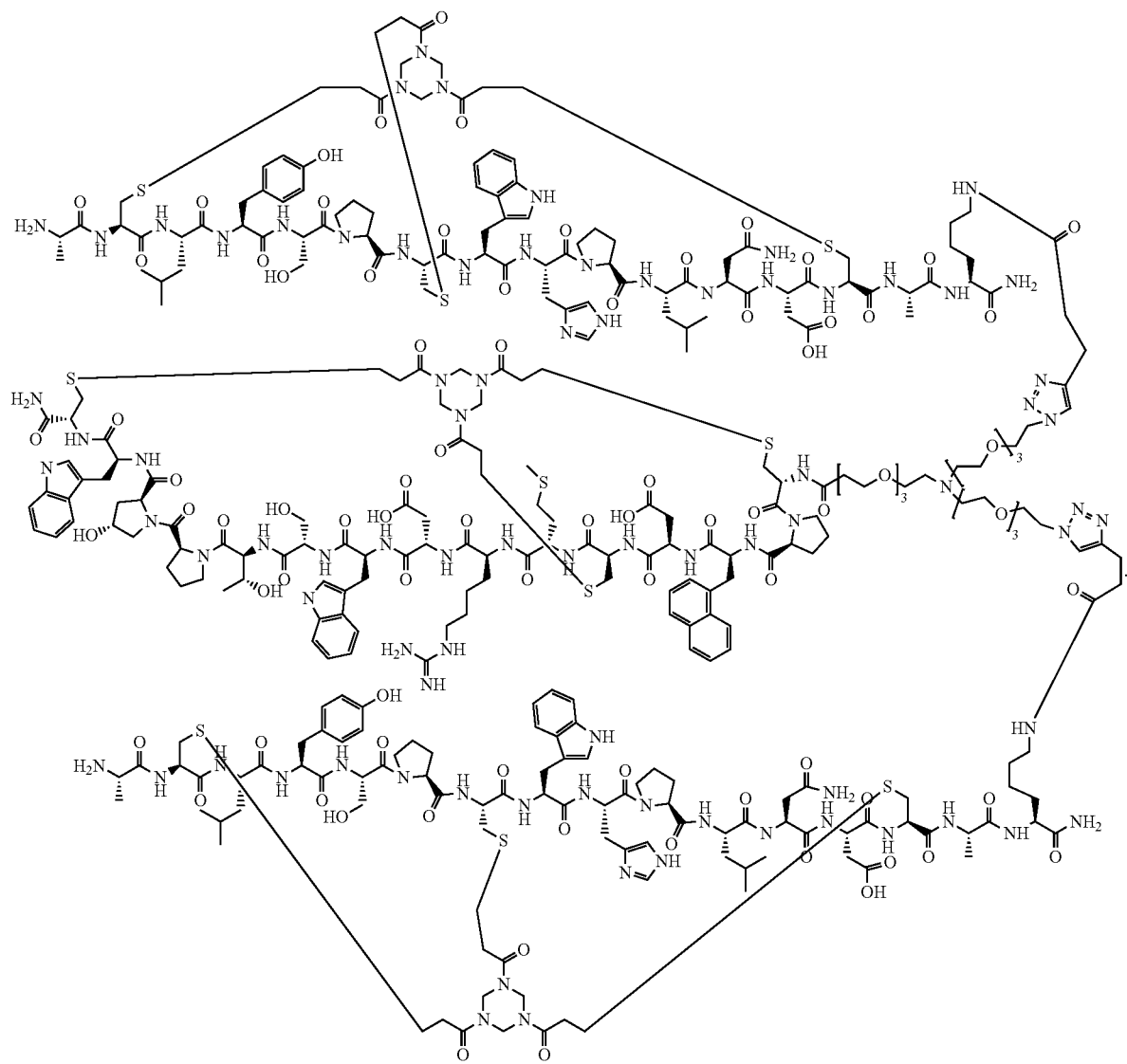

The invention claimed is:

1. A peptide ligand specific for OX40 comprising a polypeptide and a molecular scaffold, wherein the polypeptide comprises the amino acid sequence selected from the group consisting of:

$C_i$ILW$C_{ii}$LPEPHDE$C_{iii}$;  (SEQ ID NO: 1)

$C_i$A$^K/_S^N/_E$$C_{ii}$DPFWYQFY$C_{iii}$;  (SEQ ID NO: 2)

$C_i$AKN$C_{ii}$DPFWYQFY$C_{iii}$;  (SEQ ID NO: 3)

$C_i$ASE$C_{ii}$PPFWYQFY$C_{iii}$;  (SEQ ID NO: 4)

$C_i^{L}/_N$YSP$C_{ii}$WHPLN$^D/_K$$C_{iii}$;  (SEQ ID NO: 5)

$C_i$LYSP$C_{ii}$WHPLND$C_{iii}$;  (SEQ ID NO: 6)

$C_i$NYSP$C_{ii}$WHPLNK$C_{iii}$;  (SEQ ID NO: 7)

$C_i$WYEYD$C_{ii}$NNWER$C_{iii}$;  (SEQ ID NO: 8)

$C_i$VIRYSP$C_{ii}$SHYLN$C_{iii}$;  (SEQ ID NO: 9)

$C_i$DYSPWWHP$C_{ii}$NHI$C_{iii}$;  (SEQ ID NO: 10)

$C_i$DA$C_{ii}$LYPDYY$C_{iii}$;  (SEQ ID NO: 12)

$C_i$RLW$C_{ii}$IPAPTDD$C_{iii}$;  (SEQ ID NO: 13)

$C_i$TMW$C_{ii}$IPAKGDW$C_{iii}$;  (SEQ ID NO: 14)

$C_i$MLW$C_{ii}$LPAPTDE$C_{iii}$;  (SEQ ID NO: 15)

$C_i$ILW$C_{ii}$LPEPPDE$C_{iii}$;  (SEQ ID NO: 16)

$C_i$LLW$C_{ii}$IPNPDDN$C_{iii}$;  (SEQ ID NO: 17)

$C_i$WLW$C_{ii}$VPNPDDT$C_{iii}$;  (SEQ ID NO: 18)

$C_i$VLW$C_{ii}$TPYPGDD$C_{iii}$;  (SEQ ID NO: 19)

$C_i$ALW$C_{ii}$IPDPQDE$C_{iii}$;  (SEQ ID NO: 20)

$C_i$TLW$C_{ii}$IPDASDS$C_{iii}$;  (SEQ ID NO: 21)

$C_i$QLW$C_{ii}$IPDADDD$C_{iii}$;  (SEQ ID NO: 22)

$C_i$QLW$C_{ii}$VPEPGDS$C_{iii}$;  (SEQ ID NO: 23)

$C_i$ALW$C_{ii}$IPEESDD$C_{iii}$;  (SEQ ID NO: 24)

$C_i$VLW$C_{ii}$IPEPQDK$C_{iii}$;  (SEQ ID NO: 25)

$C_i$TLW$C_{ii}$IPDPDDS$C_{iii}$;  (SEQ ID NO: 26)

$C_i$RLW$C_{ii}$VPKAEDY$C_{iii}$;  (SEQ ID NO: 27)

$C_i$TKP$C_{ii}$IAYYNQS$C_{iii}$;  (SEQ ID NO: 28)

$C_i$MNP$C_{ii}$IAYYQQE$C_{iii}$;  (SEQ ID NO: 29)

$C_i$TNA$C_{ii}$VAYYHQA$C_{iii}$;  (SEQ ID NO: 30)

$C_i$SDP$C_{ii}$ISYYNQA$C_{iii}$;  (SEQ ID NO: 31)

$C_i$DPP$C_{ii}$DPFWYAFY$C_{iii}$;  (SEQ ID NO: 32)

$C_i$PDD$C_{ii}$DPFWYNFY$C_{iii}$;  (SEQ ID NO: 33)

$C_i$RYSP$C_{ii}$YHPHN$C_{iii}$;  (SEQ ID NO: 34)

$C_i$LYSP$C_{ii}$NHPLNS$C_{iii}$;  (SEQ ID NO: 35)

$C_i$EDNY$C_{ii}$FMWTPY$C_{iii}$;  (SEQ ID NO: 36)

$C_i$LDSP$C_{ii}$WHPLND$C_{iii}$;  (SEQ ID NO: 37)

$C_i$RFSP$C_{ii}$SHPLNQ$C_{iii}$;  (SEQ ID NO: 38)

$C_i$KYSP$C_{ii}$WHPLNL$C_{iii}$;  (SEQ ID NO: 39)

$C_i$RYSP$C_{ii}$WHPLNN$C_{iii}$;  (SEQ ID NO: 40)

$C_i$VWEA$C_{ii}$PEHPDQWW$C_{iii}$;  (SEQ ID NO: 42)

$C_i$STWH$C_{ii}$FWNLQEGK$C_{iii}$;  (SEQ ID NO: 43)

$C_i$EWKA$C_{ii}$EHDRERWW$C_{iii}$;  (SEQ ID NO: 44)

$C_i$RTWQ$C_{ii}$FYEWQNGH$C_{iii}$;  (SEQ ID NO: 45)

$C_i$KTWD$C_{ii}$FWASQVSE$C_{iii}$;  (SEQ ID NO: 46)

-continued $C_iSTWQC_{ii}FYDLQEGHC_{iii}$; (SEQ ID NO: 47)

$C_iTTWEC_{ii}FYDLQEGHC_{iii}$; (SEQ ID NO: 48)

$C_iETWEC_{ii}FWRLQAGEC_{iii}$; (SEQ ID NO: 49)

$C_iRTWQC_{ii}FWDLQEGLC_{iii}$; (SEQ ID NO: 50)

$C_iSTWQC_{ii}FWDSQLGAC_{iii}$; (SEQ ID NO: 51)

$C_iETWEC_{ii}FWEWQVGSC_{iii}$; (SEQ ID NO: 52)

$C_iTTWEC_{ii}FWDLQEGLC_{iii}$; (SEQ ID NO: 53)

$C_iHTWDC_{ii}FYQWQDGHC_{iii}$; (SEQ ID NO: 54)

$C_iTTWEC_{ii}FYSLQDGHC_{iii}$; (SEQ ID NO: 55)

$C_iNEDMYC_{ii}FMWMEC_{iii}$; (SEQ ID NO: 56)

$C_iLYEYDC_{ii}YTWRRC_{iii}$; (SEQ ID NO: 57)

$C_iRYEYDC_{ii}HTWQRC_{iii}$; (SEQ ID NO: 58)

$C_iWYEYDC_{ii}TTWERC_{iii}$; (SEQ ID NO: 59)

$C_iWYEYDC_{ii}RTWTRC_{iii}$; (SEQ ID NO: 60)

$C_iLYEYDC_{ii}HTWTRC_{iii}$; (SEQ ID NO: 61)

$C_iWYEYDC_{ii}RTWTFC_{iii}$; (SEQ ID NO: 62)

$C_iHGGVWC_{ii}IPNINDSC_{iii}$; (SEQ ID NO: 63)

$C_iDSPVRC_{ii}YWNTQKGC_{iii}$; (SEQ ID NO: 64)

$C_iGSPVPC_{ii}YWNTRKGC_{iii}$; (SEQ ID NO: 65)

$C_iAPFEFNC_{ii}YTWRPC_{iii}$; (SEQ ID NO: 66)

$C_iRVLYSPC_{ii}YHWLNC_{iii}$; (SEQ ID NO: 67)

$C_iSIMYSPC_{ii}EHPHNHC_{iii}$; (SEQ ID NO: 68)

$C_iDKWEPDHLC_{ii}YWWC_{iii}$; (SEQ ID NO: 69)

$C_iDAWPETHVC_{ii}YWWC_{iii}$; (SEQ ID NO: 70)

$C_iDEYTPEHLC_{ii}YWWC_{iii}$; (SEQ ID NO: 71)

$C_iWINYSISPC_{ii}YVGEC_{iii}$; (SEQ ID NO: 72)
and $C_iRYEYPEHLC_{ii}YTWQC_{iii}$; (SEQ ID NO: 73)

wherein $C_i$, $C_{ii}$ and $C_{iii}$ represent first, second and third cysteine residues, respectively, and wherein the molecular scaffold forms covalent bonds with $C_i$, $C_{ii}$ and $C_{iii}$ of the polypeptide such that at least two polypeptide loops are formed on the molecular scaffold, or a pharmaceutically acceptable salt thereof, or a modified derivative selected from the group consisting of N-terminal modification, C-terminal modification, and replacement of one or more L-amino acid residues with D-amino acid residues.

2. The peptide ligand as defined in claim 1, wherein the polypeptide comprises the amino acid sequence selected from the group consisting of:
  A-(SEQ ID NO: 1)-A-[Sar6]-[KBiot] (herein referred to as BCY10551);
  A-(SEQ ID NO: 1)-A (herein referred to as BCY10371);
  A-(SEQ ID NO: 3)-A-[Sar6]-[KBiot] (herein referred to as BCY10552);
  [Biot]-G-[Sar5]-A-(SEQ ID NO: 3)-A (herein referred to as BCY10479);
  A-(SEQ ID NO: 3)-A (herein referred to as BCY10378);
  [Biot]-G-[Sar5]-A-(SEQ ID NO: 4)-A (herein referred to as BCY11371);
  A-(SEQ ID NO: 4)-A (herein referred to as BCY10743);
  [Biot]-G-[Sar5]-A-(SEQ ID NO: 6)-A (herein referred to as BCY10482);
  A-(SEQ ID NO: 6)-A-[Sar6]-[KBiot] (herein referred to as BCY10549);
  A-(SEQ ID NO: 6)-A-K(Pya) (herein referred to as BCY11607);
  Ac-A-(SEQ ID NO: 6)-A-K(Pya) (hereinafter referred to as BCY12708);
  A-(SEQ ID NO: 6)-A (herein referred to as BCY10351);
  A-(SEQ ID NO: 7)-A-[Sar6]-[KBiot] (herein referred to as BCY11501);
  A-(SEQ ID NO: 7)-A (herein referred to as BCY10729);
  A-(SEQ ID NO: 8)-A-[Sar6]-[KBiot] (herein referred to as BCY10550);
  A-(SEQ ID NO: 8)-A (herein referred to as BCY10361);
  A-(SEQ ID NO: 9)-A-[Sar6]-[KBiot] (herein referred to as BCY10794);
  A-(SEQ ID NO: 9)-A (herein referred to as BCY10349);
  [Biot]-G-[Sar5]-A-(SEQ ID NO: 10)-A (herein referred to as BCY11369);
  A-(SEQ ID NO: 10)-A (herein referred to as BCY10331);
  A-(SEQ ID NO: 12)-A (herein referred to as BCY10375);
  A-(SEQ ID NO: 13)-A (herein referred to as BCY10364);
  A-(SEQ ID NO: 14)-A (herein referred to as BCY10365);
  A-(SEQ ID NO: 15)-A (herein referred to as BCY10366);
  A-(SEQ ID NO: 16)-A (herein referred to as BCY10367);
  A-(SEQ ID NO: 17)-A (herein referred to as BCY10368);
  A-(SEQ ID NO: 18)-A (herein referred to as BCY10369);
  A-(SEQ ID NO: 19)-A (herein referred to as BCY10374);
  A-(SEQ ID NO: 20)-A (herein referred to as BCY10376);
  A-(SEQ ID NO: 21)-A (herein referred to as BCY10737);
  A-(SEQ ID NO: 22)-A (herein referred to as BCY10738);
  A-(SEQ ID NO: 23)-A (herein referred to as BCY10739);
  A-(SEQ ID NO: 24)-A (herein referred to as BCY10740);
  A-(SEQ ID NO: 25)-A (herein referred to as BCY10741);
  A-(SEQ ID NO: 26)-A (herein referred to as BCY10742);

A-(SEQ ID NO: 27)-A (herein referred to as BCY10380);
A-(SEQ ID NO: 28)-A (herein referred to as BCY10370);
A-(SEQ ID NO: 29)-A (herein referred to as BCY10372);
A-(SEQ ID NO: 30)-A (herein referred to as BCY10373);
A-(SEQ ID NO: 31)-A (herein referred to as BCY10379);
A-(SEQ ID NO: 32)-A (herein referred to as BCY10377);
A-(SEQ ID NO: 33)-A (herein referred to as BCY10744);
A-(SEQ ID NO: 34)-A (herein referred to as BCY10343);
A-(SEQ ID NO: 35)-A (herein referred to as BCY10350);
A-(SEQ ID NO: 36)-A (herein referred to as BCY10352);
A-(SEQ ID NO: 37)-A (herein referred to as BCY10353);
A-(SEQ ID NO: 38)-A (herein referred to as BCY10354);
A-(SEQ ID NO: 39)-A (herein referred to as BCY10730);
A-(SEQ ID NO: 40)-A (herein referred to as BCY10731);
A-(SEQ ID NO: 41)-A (herein referred to as BCY10339);
A-(SEQ ID NO: 42)-A (herein referred to as BCY10340);
A-(SEQ ID NO: 43)-A (herein referred to as BCY10342);
A-(SEQ ID NO: 44)-A (herein referred to as BCY10345);
A-(SEQ ID NO: 45)-A (herein referred to as BCY10347);
A-(SEQ ID NO: 46)-A (herein referred to as BCY10348);
A-(SEQ ID NO: 47)-A (herein referred to as BCY10720);
A-(SEQ ID NO: 48)-A (herein referred to as BCY10721);
A-(SEQ ID NO: 49)-A (herein referred to as BCY10722);
A-(SEQ ID NO: 50)-A (herein referred to as BCY10723);
A-(SEQ ID NO: 51)-A (herein referred to as BCY10724);
A-(SEQ ID NO: 52)-A (herein referred to as BCY10725);
A-(SEQ ID NO: 53)-A (herein referred to as BCY10726);
A-(SEQ ID NO: 54)-A (herein referred to as BCY10727);
A-(SEQ ID NO: 55)-A (herein referred to as BCY10728);
A-(SEQ ID NO: 56)-A (herein referred to as BCY10360);
A-(SEQ ID NO: 57)-A (herein referred to as BCY10363);
A-(SEQ ID NO: 58)-A (herein referred to as BCY10732);
A-(SEQ ID NO: 59)-A (herein referred to as BCY10733);
A-(SEQ ID NO: 60)-A (herein referred to as BCY10734);
A-(SEQ ID NO: 61)-A (herein referred to as BCY10735);
A-(SEQ ID NO: 62)-A (herein referred to as BCY10736);
A-(SEQ ID NO: 63)-A (herein referred to as BCY10336);
A-(SEQ ID NO: 64)-A (herein referred to as BCY10337);
A-(SEQ ID NO: 65)-A (herein referred to as BCY10338);
A-(SEQ ID NO: 66)-A (herein referred to as BCY10346);
A-(SEQ ID NO: 67)-A (herein referred to as BCY10357);
A-(SEQ ID NO: 68)-A (herein referred to as BCY10362);
A-(SEQ ID NO: 69)-A (herein referred to as BCY10332);
A-(SEQ ID NO: 70)-A (herein referred to as BCY10717);
A-(SEQ ID NO: 71)-A (herein referred to as BCY10718);
A-(SEQ ID NO: 72)-A (herein referred to as BCY10334); and
A-(SEQ ID NO: 73)-A (herein referred to as BCY10719),
wherein Pya represents 4-pentynoyl moiety, and Biot represents biotin, or a pharmaceutically acceptable salt thereof, or a modified derivative selected from the group consisting of N-terminal modification, C-terminal modification, and replacement of one or more L-amino acid residues with D-amino acid residues.

3. The peptide ligand as defined in claim 1, wherein said peptide ligand is selected from the group consisting of BCY11607, BCY10551, BCY10552, BCY10479, BCY11371, BCY10482, BCY10549, BCY11501, BCY10550, BCY10794 and BCY11369.

4. The peptide ligand as defined in claim 3, wherein said peptide ligand is selected from the group consisting of BCY10551, BCY11371 and BCY10549.

5. The peptide ligand as defined in claim 3, wherein said peptide ligand is BCY10549.

6. The peptide ligand as defined in claim 1, wherein the molecular scaffold is 1,1',1"-(1,3,5-triazinane-1,3,5-triyl) triprop-2-en-1-one (TATA).

7. The peptide ligand as defined in claim 1, wherein the peptide ligand is the free acid, or a pharmaceutically acceptable salt selected from sodium, potassium, calcium or ammonium salt.

8. A pharmaceutical composition comprising the peptide ligand as defined in claim 1, in combination with one or more pharmaceutically acceptable excipients.

9. A drug conjugate comprising the peptide ligand as defined in claim 1, conjugated to one or more effector and/or functional groups.

10. A multimeric binding complex comprising at least two peptide ligands, wherein at least one peptide ligand is the peptide ligand specific for OX40 as defined in claim 1.

11. The multimeric binding complex as defined in claim 10, wherein each peptide ligand is connected to a central hinge moiety by a spacer group.

12. The multimeric binding complex as defined in claim 10, which comprises a compound of formula (I):

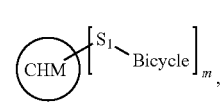

wherein CHM represents a central hinge moiety;
S₁ represents a spacer group;
Bicycle represents the peptide ligand specific for OX40; and
m represents an integer selected from 2 to 10.

13. The multimeric binding complex as defined in claim 10, wherein said peptide ligands are specific for the same target.

14. The multimeric binding complex as defined in claim 10, wherein the multimeric binding complex comprises at least two identical peptide ligands.

15. The multimeric binding complex as defined in claim 14, wherein the multimeric binding complex comprises four identical peptide ligands.

16. The multimeric binding complex as defined in claim 15, wherein the multimeric binding complex comprises four BCY10549 peptide ligands.

17. The multimeric binding complex as defined in claim 15, wherein the multimeric binding complex comprises the tetrameric complex BCY12019.

18. The multimeric binding complex as defined in claim 10, wherein the multimeric binding complex comprises at least two different peptide ligands.

19. The multimeric binding complex as defined in claim 10, wherein said peptide ligands are specific for different targets.

20. The multimeric binding complex as defined in claim 10, wherein at least one of said peptide ligands is the peptide ligand specific for OX40, and at least one of said peptide ligands binds to a different component on an immune cell.

21. The multimeric binding complex as defined in claim 20, wherein the different component on an immune cell is cluster of differentiation 137 (CD137).

22. The multimeric binding complex as defined in claim 10, wherein at least one of said peptide ligands is the peptide ligand specific for OX40, and at least one second peptide ligand binds to a component present on a cancer cell, and optionally further comprising a third peptide ligand binds to a different component on an immune cell.

23. The multimeric binding complex as defined in claim 22, wherein the second peptide ligand binds to ephrin type-A receptor 2 (EphA2), programmed death ligand-1 (PD-L1), Nectin-4 or prostate-specific membrane antigen (PSMA).

24. The multimeric binding complex as defined in claim 23, wherein the second peptide ligand comprises a Nectin-4 binding bicyclic peptide ligand comprising the amino acid sequence:
CP[1Nal][dD]CM[HArg]DWSTP[HyP]WC (SEQ ID NO: 11; hereinafter referred to as BCY8116), wherein 1Nal represents 1-naphthylalanine, HArg represents homoarginine, and HyP represents hydroxyproline, or a pharmaceutically acceptable salt thereof, or a modified derivative selected from the group consisting of N-terminal modification, C-terminal modification, and replacement of one or more L-amino acid residues with D-amino acid residues.

25. The multimeric binding complex as defined in claim 24, wherein the second peptide ligand is selected from the group consisting of a polyethylene glycol (PEG)12 derivative of BCY8116, a PEG5 derivative of BCY8116, and a trifunctional PEG3 derivative of BCY8116.

26. The multimeric binding complex as defined in claim 22, which is selected from the group consisting of BCY12141, BCY12721 and BCY12697:

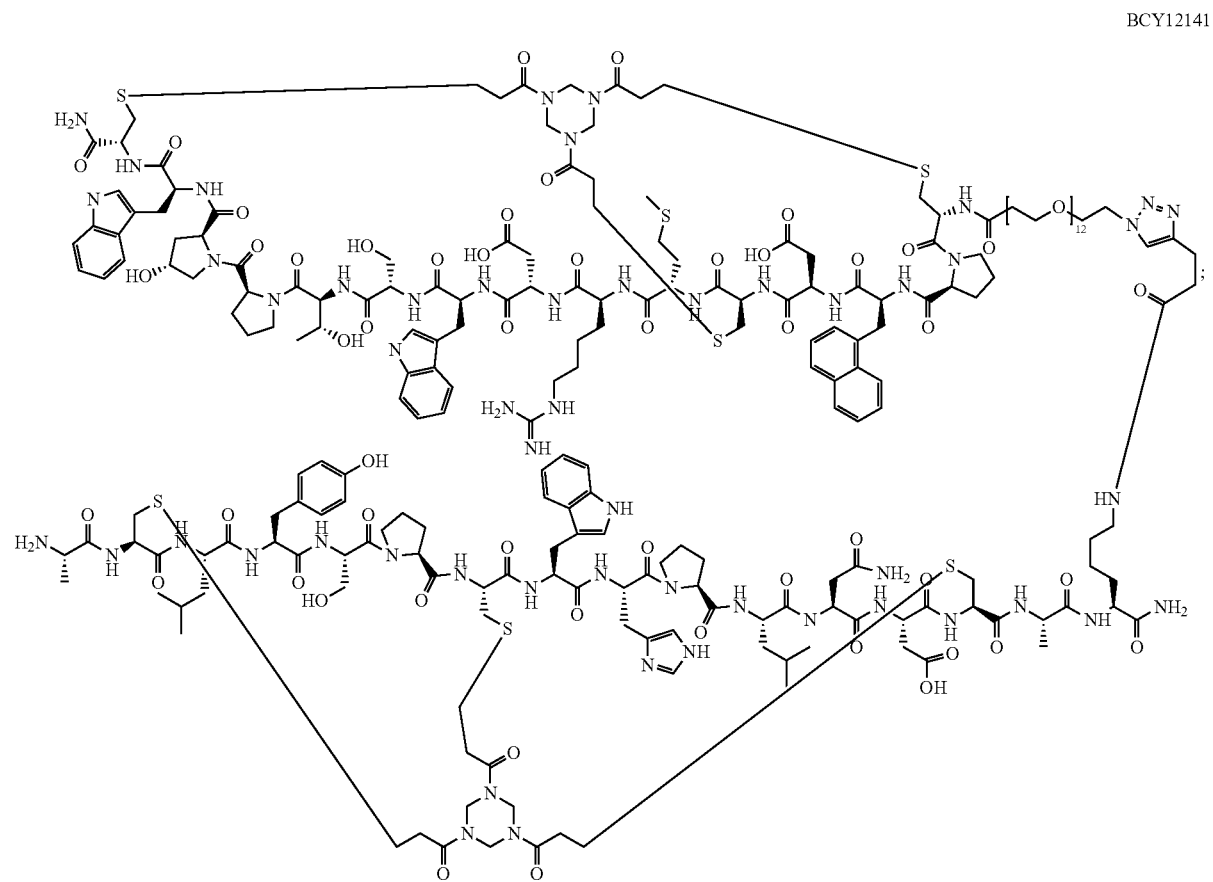

BCY12141

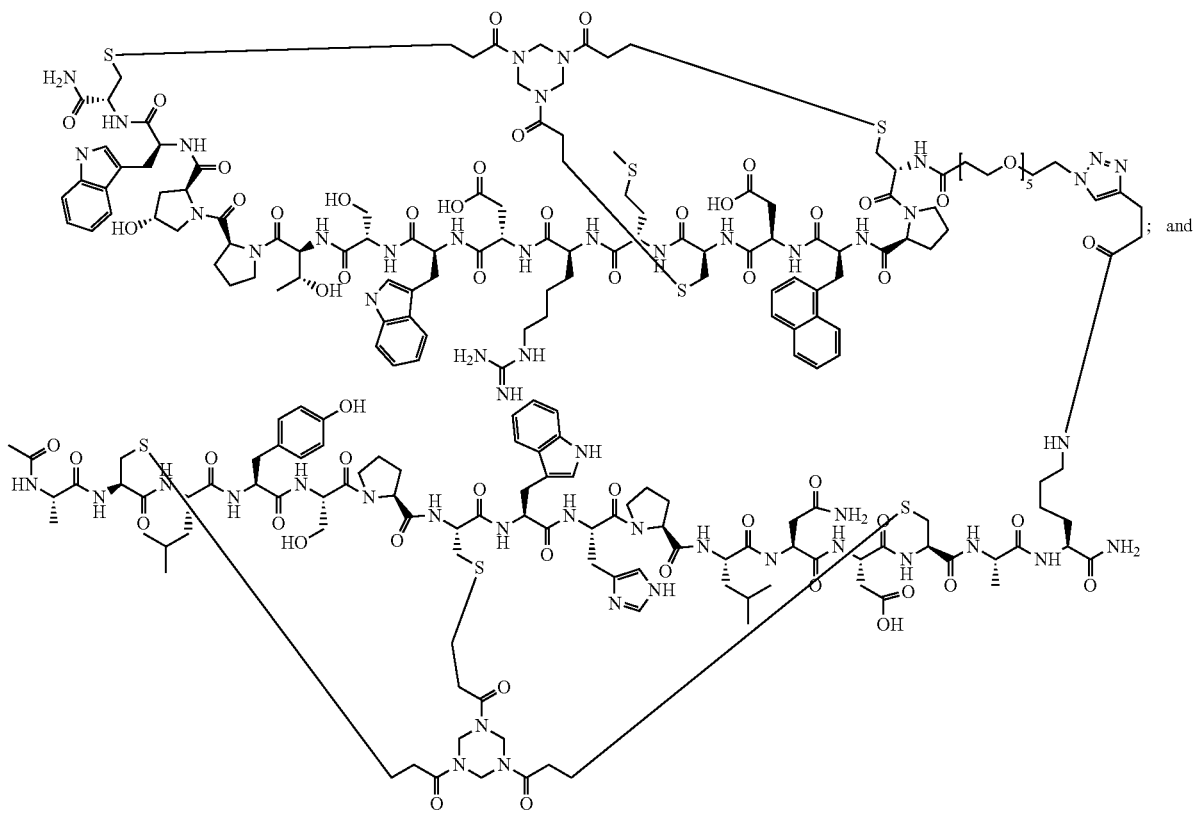
BCY12721